United States Patent
Lu et al.

(10) Patent No.: US 7,132,234 B2
(45) Date of Patent: Nov. 7, 2006

(54) METHODS AND COMPOSITIONS FOR THE IDENTIFICATION OF ANTI-POXVIRUS AGENTS

(75) Inventors: Henry H. Lu, Foster City, CA (US); Jianing Huang, Foster City, CA (US); Donald G. Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/975,285

(22) Filed: Oct. 27, 2004

(65) Prior Publication Data

US 2005/0180994 A1    Aug. 18, 2005

Related U.S. Application Data

(60) Provisional application No. 60/620,774, filed on Oct. 20, 2004, provisional application No. 60/515,279, filed on Oct. 28, 2003.

(51) Int. Cl.
| | |
|---|---|
| *C12Q 1/70* | (2006.01) |
| *C12Q 1/48* | (2006.01) |
| *C12Q 1/18* | (2006.01) |
| *C12N 9/10* | (2006.01) |
| *A61K 49/00* | (2006.01) |

(52) U.S. Cl. .............................. 435/5; 435/15; 435/32; 435/193; 424/9.2

(58) Field of Classification Search .................... 435/5, 435/15, 29, 32, 183, 184, 194, 193; 424/9.1, 424/9.2
See application file for complete search history.

(56) References Cited

U.S. PATENT DOCUMENTS

2002/0042083 A1    4/2002    Issakani

FOREIGN PATENT DOCUMENTS

WO    WO 01/75145    * 10/2001

OTHER PUBLICATIONS

Mansouri et al (Journal of Virology 77:1427-1440, Jan. 2003).*
Fruh et al (Virus Research 88 :55-69, 2002).*
Afonso et al, The Genome of Fowlpox Virus, J. Virlolgy 74: 3815-3831, 2000.
Alcami, et al, Poxviruses: Capturing Cytokines and Chemokines, 1998 Semin. Virol. 8,419-427.
Antoine et al, The Complete Genomic Sequence of the Modified Vaccinia Ankara Strain: Comparison with Other Orthopoxviruses, Virology 244:365-96, 1998.
Brick et al, Ectromelia Virus Virulence Factor P28 Acts Upstream of Caspase-3 in Response to UV Light-Induced Apoptosis J. General Virology 81: 1087-1097, 2000.
Goebel, et al, The Complete DNA Sequence of Vaccinia Virus Virology, 1990 Virology 179, 247-266, 517-563.
Jensen et al., Identification of the Major Membrane and Core Proteins of Vaccinia Virus by Two-Dimensional Electrophoresis, 1996, J. Virol., 70, 7485-7497.
McCraith et al, Genome-Wide Analysis of Vaccinia Virus Protein-Protein Interactions, Proc Natl Acad Sci, 2000, 97:4879-84.
McFadden et al, How Poxviruses Oppose Apoptosis, 1998, Semin. Virol. 8, 429-442.
Perkus et al, Deletion of 55 Open Reading Frames From the Termini of Vaccinia Virus, Virology, 1991, 180:406-10.
Senkevich et al, Ectromelia Virus Ring Finger Protein is Localized in Virus Factories and is Required for Virus Replication in Macrophages, J. Virology 69: 4103-4111 1995.
Senkevich et al, A Poxvirus Protein with a Ring Zinc Finger Motif is of Crucial Importance for Virulence, Virology, 1994 198: 118-128.
Takahashi et al., N-Terminal Amino Acid Sequences of Vaccinia Virus Structural Proteins, 1994 Virology 202, 844-852.
Upton et al, Screening Predicted Coding Regions in Poxvirus Genomes, Virus Genes, 20:159-64, 2000.
Wong et al, 2003, Drug Discovery in the Ubiquitin Regulatory Pathway, Drug Discovery Today, 8:746-754.
Brick et al., Shope Fibroma Virus Ring Finger Protein N1R Binds DNA and Inhibits Apoptosis, Virology, 1998, 249: 42-51.
Shchelkunov,S.N., Genes of Variola and Vaccinia Viruses Necessary to Overcome Thehost Protective Mechanisms, 1993, GenBank Accession No. X69198.

* cited by examiner

*Primary Examiner*—Mary E. Mosher
(74) *Attorney, Agent, or Firm*—James S. Keddie; Carol L. Francis; James J. Diehl

(57) ABSTRACT

The invention provides methods for identifying an anti-poxviral agents. In many embodiments, the methods involve contacting a poxviral p28 polypeptide with a candidate agent, and determining an effect of the agent on a ubiquitin ligase activity of the p28 polypeptide. The effect of the agent may be determined using a variety of different cell based or biochemical assays, such as polyubiquitylation assays and cell viability assays. The invention also provides methods for modulating poxvirus pathogenicity in a cell, and methods of treating an individual infected with a poxvirus. The subject methods find use in a variety of drug discovery, research and military applications.

32 Claims, 10 Drawing Sheets

3A

3B

4A

4B

4C 1 2 3 4

Anti-FLAG

1, E1+ubc5c

2, E1+ubc5c+Evp28C173A

3, E1+ubc5c+Evp28H199C

4, E1+ubc5c+Evp28wt

Identification of Inhibitors of EVp28 ligase activity

METHODS AND COMPOSITIONS FOR THE IDENTIFICATION OF ANTI-POXVIRUS AGENTS

This application claims the benefit of provisional application 60/515,279, filed Oct. 28, 2003, and 60/620,774, filed Oct. 20, 2004.

FIELD OF THE INVENTION

The present invention relates generally to the field of antipoxvirus agents, particularly agents that act by modulating the ubiquitin ligase activity of a poxvirus p28 protein.

BACKGROUND OF THE INVENTION

Smallpox is a serious, highly contagious, and frequently fatal infectious disease for which there is no specific treatment, and for which the only prevention is vaccination. Two clinical forms of smallpox have been described variolaminor and *variola major*, with the *variola major* form of smallpox being the more common and severe. There are four types of *variola major* smallpox: ordinary (the most frequent); modified (mild and occurring in previously vaccinated persons); flat; and hemorrhagic. Overall, *variola major* has a case-fatality rate of about 30%.

The most virulent form of smallpox, hemorrhagic smallpox, destroys the linings of the throat, stomach, intestines, rectum, and vagina and causes black, unclotted blood to ooze from the mouth and other body orifices. Because hemorrhagic smallpox has a much shorter incubation period than other forms of smallpox, it is likely not to be initially recognized as smallpox when first presented to medical care. As such, most victims die prior to a correct diagnosis, often before they are quarantined. Smallpox vaccination also does not provide much protection, if any, against hemorrhagic smallpox since hemorrhagic smallpox causes death of 94% of vaccinated patients. Hemorrhagic smallpox causes death in 99% of unvaccinated patients.

Because of the deadliness of smallpox, biological weapons, or so called "weapons of mass destruction" that are based on the etiological agent that causes smallpox, variola virus, are currently thought to be a great threat. Accordingly, there is an urgent need for methods and compositions for treating and preventing smallpox.

However, despite intense research, the primary treatments and preventions for smallpox are either not effective or not practical in the event of an outbreak from a virulent strain of smallpox.

The primary therapeutic tools for the control and eradication of smallpox include a live virus vaccine to prevent disease, and a vaccinia immune globulin (VIG) to treat disseminated infections.

The smallpox vaccine (live vaccinia virus) has many side-effects including: adverse reactions, scarring, ocular autoinoculation, myocardial infarction and dissemination in immunocompromised persons. Cell culture-derived vaccines, are being developed; however, these vaccines are also live viruses and pose many of the same drawbacks that plague the current vaccine. Accordingly, the public at large, the healthcare community and the military have been resistant to smallpox vaccinations because the risks of side-effects appear to outweigh the advantages. Further, as discussed above, current vaccination methods are practically ineffective against hemorrhagic smallpox or its derivatives, the agents that would most likely be used in biological weapons.

The existing vaccinia immune globulin products are derived from human donors who have been vaccinated with vaccinia virus (the vaccine for smallpox). As with all human products, the existing VIG must be tested exhaustively for blood borne human pathogens such as human immunodeficiency virus and hepatitis B. Therefore, the existing VIG suffers from several drawbacks including the necessity for using human volunteers, i.e. the use of a live virus as an immunogen which could cause infectious lesions that scar in healthy individuals and severe disseminated life-threatening infection in immunocompromised individuals. And, despite continuous screening of the donor population to assure consistency which is very expensive, product lots can vary significantly between batches and geographic regions.

Accordingly, the primary treatment for smallpox infection is not practical in most situations. In addition, since vaccinia virus is an ineffective vaccine for hemorrhagic smallpox, it is unlikely vaccinia immune globulin products will be effective against hemorrhagic smallpox.

Research into the biology of smallpox is intensive. For example, the genome of variola virus has been sequenced, and it is about 185 kbp in length and is predicted to contain over 200 proteins. Many proteins involved in transcription and DNA replication, and about 30 proteins that form the core and membrane components of virus particles have been identified. Other viral proteins have been identified that are thought to interact with host components to facilitate virus dissemination, prevent apoptosis, and attenuate immune responses. However, although well over 10 years have passed since the genome of vaccinia virus was sequenced, the biochemical function of most viral proteins, in particular, p28, which has been shown to be required for viral pathogenesis, remain elusive. The development of anti-viral assays and the discovery of effective drugs to combat smallpox infection have been slow.

Accordingly, despite great effort and the ever-present threat of a serious hemorrhagic smallpox outbreak, an effective, practical therapy (including prevention and treatment) for smallpox, is not currently available. Accordingly, there is a great need for new assays to discover drugs for the treatment of smallpox, and a great need for new smallpox therapies, particularly those that may be deployed rapidly, safely and in great number. This invention meets this need, and others.

Literature of interest includes Afonso et al, J. Virology 74: 3815–3831, 2000; Brick et al, J. General Virology 81: 1087–1097, 2000; Senkevich et al, Virology 198: 118–128, 1994; Senkevich et al, J. Virology 69: 4103–4111 1995; Antoine et al, Virology 244:365–96, 1998; Upton et al, Virus Genes 20: 159–64, 2000; Perkus et al, Virology 180:406–10, 1991; McCraith et al, Proc Natl Acad Sci 97:4879–84, 2000; Goebel, et al, 1990 Virology 179, 247–266, 517–563; Jensen et al. 1996 J. Virol. 70, 7485–7497; Takahashi et al 1994 Virology 202, 844–852; Alcami, et al, 1998 Semin. Virol. 8,419–427; Wong et al 2003 Drug Discovery Today 8:746–754; McFadden, et al, 1998 Semin. Virol. 8, 429–442; GenBank Accession number X69198 and published US patent application U.S. 20020042083.

SUMMARY OF THE INVENTION

The invention provides methods for identifying an anti-poxviral agents. In many embodiments, the methods involve contacting a poxviral p28 polypeptide with a candidate agent, and determining an effect of the agent on a ubiquitin ligase activity of the p28 polypeptide. The effect of the agent may be determined using a variety of different cell based or biochemical assays, such as polyubiquitylation assays and cell viability assays. The invention also provides methods for modulating poxvirus pathogenicity in a cell, and methods of treating an individual infected with a poxvirus. The subject methods find use in a variety of drug discovery, research and military applications.

BRIEF DESCRIPTION OF THE DRAWINGS

The invention is best understood from the following detailed description when read in conjunction with the accompanying drawings. It is emphasized that, according to common practice, the various features of the drawings are not ID-scale. On the contrary, the dimensions of the various features are arbitrarily expanded or reduced for clarity. Included in the drawings are the following figures.

DEFINITIONS

Figure 1A:
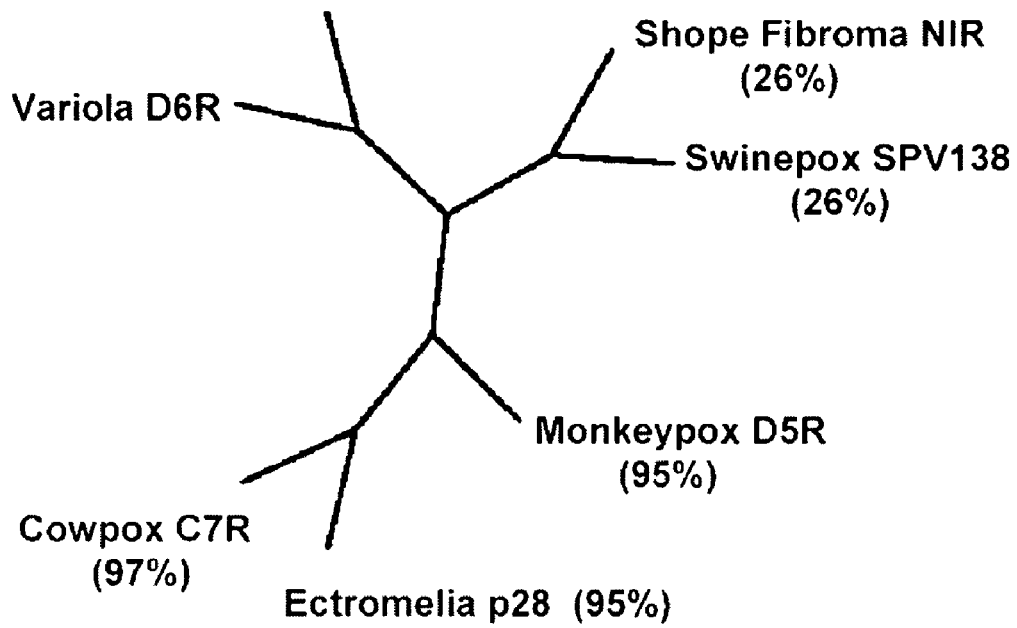
FIGS. 1A and 1B show sequence analysis of p28 and related polypeptides. (1A) Phylogenetic tree of p28 proteins encoded by poxvirus genus *Orthopoxviruses* (Variola ORF D6R, Monkeypox D5R, Ectromelia p28, Cowpox ORF C7R, and Camelpox ORF gp013), and p28 homologs encoded by poxvirus genera *Leporipoxvirus* (Shope fibroma virus ORF N1R) and *Suipoxvirus* (Swinepox virus ORF SPV138). Amino acid sequence identities (aligned with Variola p28) are shown in parentheses. (1B) Diagram of p28 gene products encoded by Variola (VARV), Ectromelia virus (ECTV), and two culture-adapted Vaccinia virus strains (VACV MR and Ankara). The RING finger domains of ECTV or VARV p28 are shown as shaded bars. ECTV p28 amino acids differing from those of VARV p28 are indicated by vertical lines, and a missing amino acid is indicated by an asterisk in the ECTV p28 diagram. p28 equivalent gene products encoded by MR or Ankara strains of VACV have truncations and disruptions in the carboxyl domain, lacking an intact RING domain. The short filled bar at the end of p28 of VACV Ankara represents a sequence with no homology to other p28 sequences.

Unless defined otherwise, all technical and scientific terms used herein have the same meaning as commonly understood by one of ordinary skill in the art to which this invention belongs. Still, certain elements are defined below for the sake of clarity and ease of reference.

"Ubiquitylated" or "ubiquitylation" in reference to a protein is meant to encompass proteins modified by conjugation to a ubiquitin (Ub) or a ubiquitin-like modifier (Ubl).

By "ubiquitin agents" is meant molecules, e.g., proteins, involved in ubiquitination. Ubiquitin agents can include ubiquitin activating agents, ubiquitin ligating agents and ubiquitin conjugating agents. In addition, ubiquitin agents can include ubiquitin moieties as described below.

"Assay components" as used herein generally comprise, at least a ubiquitin moiety, a ubiquitin activating agent, a ubiquitin conjugating agent, a ubiquitin ligating agent, and, in some embodiments, a substrate protein for ubiquitylation. In the methods of the invention, poxvirus p28 is used as a ubiquitin ligating agent, and the assay components are combined with a candidate agent to assess the effect of the candidate agent the ubiquitin ligase activity of p28.

The term "ubiquitylation reaction conditions" refers to reaction conditions in which assay components ubiquitylate a substrate. The substrate may be one of the assay components (e.g., the ubiquitin ligating agent can also serve as the substrate protein for ubiquitylation). Conditions suitable for ubiquitylation are varied, are very well known in the art and are described in great detail in published US Patent Application U.S. 20020042083 and Wong et al (Drug Discovery Today 8:746–754, 2003). Suitable conditions may be in a cell or in a cell free environment.

"Isolated" means that the recited material is unaccompanied by at least some of the material with which it is normally associated in its natural state, preferably constituting at least about 0.5%, more preferably at least about 5% by weight of the total protein in a given sample. "Purified" means that the recited material comprises at least about 75% by weight of the total protein, with at least about 80% being preferred, and at least about 90% being particularly preferred.

The terms "polypeptide" and "protein" are used interchangeably throughout the application and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. Normally, the amino acids are in the (S) or L-configuration. If non-naturally occurring side chains are used, non-amino acid substituents may be used, for example to prevent or retard in vivo degradation. Naturally occurring amino acids are normally used and the protein is a cellular protein that is either endogenous or expressed recombinantly.

A recombinant protein may be distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes, but is not limited to, the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

By "nucleic acid" herein is meant either DNA or RNA, or molecules which contain both deoxy- and ribonucleotides. The nucleic acids include genomic DNA, cDNA and oligonucleotides including sense and anti-sense nucleic acids. Also siRNA are included. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than invitro manipulations; however, such nucleic acids, once produced recombinantly, although subsequently replicated non-recombinantly, are still considered recombinant for the purposes of the invention.

Other definitions of terms appear throughout the specification.

DETAILED DESCRIPTION OF THE INVENTION

The invention provides methods for identifying an antipoxviral agents. In many embodiments, the methods involve contacting a poxviral p28 polypeptide with a candidate agent, and determining an effect of the agent on a ubiquitin ligase activity of the p28 polypeptide. The effect of the agent may be determined using a variety of different cell based or cell-free biochemical assays, such as polyubiquitylation assays and cell viability assays. The invention also provides methods for modulating poxvirus pathogenicity (e.g., replication) in a cell, and methods of treating an individual infected with a poxvirus. The subject methods find use in a variety of drug discovery, research and military applications.

Before the present invention is described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Although any methods and materials similar or equivalent to those described herein can be used in the practice or testing of the present invention, exemplary and preferred methods and materials are now described. All publications mentioned herein are incorporated herein by reference to disclose and describe the methods and/or materials in connection with which the publications are cited.

It must be noted that as used herein and in the appended claims, the singular forms “a”, “an”, and “the” include plural referents unless the context clearly dictates otherwise. Thus, for example, reference to “a candidate agent” includes a plurality of such candidate agents and reference to “the cell” includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In describing this invention, screening assays will be described first, followed by a description of methods of modulating poxvirus pathogenicity in a cell. Finally, methods of treating poxvirus infections and kits are described.

Screening Methods

In one aspect, the invention features screening methods for, for example, identification of agents that modulate ubiquitin ligase activity of poxvirus p28 polypeptide. Components for use in these screening methods are described below, and then various exemplary screening formats are provided.

Assay Components

As noted above, “ubiquitin agents' as used herein refers to a collection of proteins that facilitates attachment of a ubiquitin moiety to a target protein via a ubiquitin ligase. The following section describes the various ubiquitin agents that may be present in the screening assays of the invention. In most embodiments, the ubiquitin ligase is a poxvirus p28 protein. This poxvirus p28 protein, because it can ubiquitylate itself, may also be the target protein. A discussion of many of these assay components may also be found in Wong et al (Drug Discovery Today 8:746–754, 2003) and published US Patent Application U.S. 20020042083, which are expressly incorporated herein in their entirety for all purposes.

Accordingly, assays usually include a ubiquitin, a ubiquitin activating agent, a ubiquitin conjugating agent, and a poxvirus p28 protein. In particular embodiments, the ubiquitin activating agent is usually an E1 protein, and the ubiquitin conjugating agent is usually an E2 protein.

Ubiquitin Ligating Agents

Most embodiments of the subject methods use a ubiquitin ligating agent. As used herein “ubiquitin ligating agent” refers to a ubiquitin agent, usually a protein (e.g., a ubiquitin ligating enzyme), capable of facilitating transfer or attachment of a ubiquitin from a ubiquitin conjugating agent to a target substrate molecule. In most embodiments, the ubiquitin ligating agent used in the subject methods is an E3 protein, e.g., a poxvirus p28 protein. Since certain ubiquitin ligating agents may autoubiquitylate, the ubiquitin ligating agent may also be a substrate for ubiquitylation, e.g., poxvirus p28 protein can serve as both the ubiquitin ligating agent and the substrate that is ubiquitylated.

“Poxvirus p28 protein” is a ring-zinc protein of approximately 28 kDa that is found in the genome of viruses of the Poxviridae family (“poxvirus” family). Accordingly, poxvirus p28 protein may be encoded by a genomes of Entomopoxviridae and Chordopoxvirinae viruses, including orthopoxvirus (e.g., variola, vaccinia, monkeypox, cowpox, rabbitpox, raccoon pox, tatera pox, buffalopox, camelpox, mousepox, etc.), avipoxvirus (fowlpox, canary pox, etc.), capripoxvirus (goatpox, sheeppox, lumpy skin disease, etc.) leporipoxvirus (myxoma, hare fibroma, etc.), parapoxvirus (orf, pseudo-cowpox, etc.), suipoxvirus (swinepox, etc.), molluscipoxvirus (molluscum contagiosum, etc.) and yatapoxvirus (tanapox, yaba, etc.), and others. The ectromelia (mousepox) p28 protein is generally described in Senkevich et al, (Virology 198, 118–128, 1994). The sequence of exemplary p28 proteins for use in the subject methods is set forth in the following Genbank Accessions: NP_671530.1 (Ectromelia virus EVM012), CAA64092.1 (Cowpox virus C7R protein), NP_536435.1 (Monkeypox virus D5R), NP_619812.1 (Cowpox virus CPXV023), NP_042048.1 (Variola virus D4R), AAA69414.1 (Variola virus D6R) and NP_570403.1 (Camelpox virus M-96). Unless otherwise indicated, the term “poxvirus” refers to any virus of the Poxviridae family of viruses.

Also included by the term “poxvirus p28 protein” are poxvirus p28 variants that retain ubiquitin ligase activity. In other words, the invention contemplates use of variants of the above proteins which retain a characteristic of a native ubiquitin ligating agent in being capable of facilitating transfer or attachment of a ubiquitin moiety to a target substrate protein. Guidance for which amino acids to change to produce a p28 variant that retains ligase activity can be obtained, for example, by aligning the amino acid sequences any of the poxivirus proteins listed above, identifying amino acids that are at identical positions in the proteins but are different between the proteins, and transferring the amino acids from one protein to the other. As discussed in greater detail below, the ring-finger domain is essential for ubiquitin ligase activity. Accordingly, poxvirus p28 proteins generally have an overall amino acid sequence identity of preferably greater than about 75%, more preferably greater than about 80%, even more preferably greater than about 85% and most preferably greater than 90% of an amino acid sequence provided above. In some embodiments the sequence identity will be as high as about 93% to 95% or 98%. In particular embodiments, the ring finger domain of the p28 proteins that find use in the subject methods have a high degree of sequence identity, e.g., at least 90%, at least 95%, at least 98% or at least 99% sequence identity. p28 variants having ubiquitin ligase activity are readily identified using the assays described above and below. Variants of these ubiquitin ligating agents and other components of the assays of the invention are described below in more detail.

Ubiquitin

By "ubiquitin" is meant any polypeptide which is transferred or attached to another polypeptide by ubiquitin agents. Ubiquitin as used in the assays below can be from any species of organism, usually a eukaryotic species, or any modified form thereof. In certain assays, the ubiquitin used is a mammalian ubiquitin, usually a human ubiquitin. Examples of ubiquitins suitable for use in the claimed methods are generally well known in the art, and include the human ubiquitin set forth in GenBank database PO2248 (which database entry is incorporated herein in its entirety), and the ubiquitin like modifier proteins known as NEDD8, ISGI5, SUMO1, SUMO2, SUMO3, APG12 and APG8, and the like. In many embodiments, the ubiquitin used in the subject assays is a naturally occurring allele or man-made variants of such polypeptides. Many ubiquitin polypeptides have an overall amino acid sequence identity of greater than about 75%, greater than about 80%, greater than about 85%, greater than 90% or even 93% to 95% or 98% or more of the amino acid sequence set forth in GenBank database $PO_{2248}$. Further examples of ubiquitin molecules suitable for use in the claimed invention are described below.

As used in the subject methods, the ubiquitin polypeptides that be shorter or longer than the amino acid sequence of human ubiquitin depicted above. Thus, included within the definition of ubiquitin are portions or fragments of human ubiquitin. In one embodiment herein, fragments of the human ubiquitin protein are considered ubiquitin if they can be attached to a target polypeptide by ubiquitin agents.

In addition, as is more fully outlined below, ubiquitins of the present invention may be fusion proteins. Such fusion proteins may contain a ubiquitin polypeptide operably linked to a fusion sequence, e.g., a tag. In some embodiments, the tag may be an affinity tag, such as an epitope tag (e.g., HA, c-myc, etc) or a tag for attachment to a specific substrate (e.g., poly-his, poly-his-gly, GST, MBP) etc., In other embodiments, the tag may be a reporter tag, such as a fluorescent peptide, e.g., luciferase or Green Fluorescent Peptide (GFP), or variant thereof.

In certain embodiments, the ubiquitin moiety is endogenous to the cell which is to be used in a screening assay. That is, where the assay involves the use of cells, the ubiquitin moiety is naturally expressed in the cell to be assayed. However, in an alternative embodiment, the ubiquitin moiety, as well as other proteins of the present invention, are exogenous, e.g., recombinant proteins. A "recombinant protein" is a protein made using recombinant techniques, i.e. through the expression of a recombinant nucleic acid as described below. In an exemplary embodiment, the ubiquitin moiety of the invention is made through the expression of a nucleic acid sequence corresponding to GENBANK accession number M26880 or AB003730, or a fragment thereof, and encodes the human ubiquitin, as discussed above.

Ubiquitin Activating Agents

As used herein "ubiquitin activating agent" refers to a ubiquitin agent, usually a protein (e.g., a ubiquitin activating enzyme), that transfers or attaches a ubiquitin moiety to a ubiquitin conjugating agent. Generally, the ubiquitin activating agent forms a high energy thiolester bond with ubiquitin moiety, thereby "activating" the ubiquitin moiety, and transfers or attaches the ubiquitin moiety to a ubiquitin conjugating agent (e.g., E2).

In a many embodiment the ubiquitin activating agent is an E1 protein, which can transfer or attach ubiquitin to an E2, defined below. Accordingly, E1 forms a high energy thiolester bond with ubiquitin, thereby "activating" the ubiquitin.

In exemplary embodiments, E1 proteins useful in the invention include those having the amino acid sequence of the polypeptide having ATCC accession numbers AAA61246, P22314, and CAA40296, incorporated herein by reference. E1 may be human E1. E1 is commercially available from Affiniti Research Products (Exeter, U.R.).

In further exemplary embodiments, nucleic acids which may be used for producing E1 proteins for the invention include, but are not limited to, those set forth in GenBank accession numbers M58028 and X56976, incorporated herein by reference. Variants of the cited E1 proteins, also included in the term "E1", can be made as described herein.

Further exemplary ubiquitin activating agents include those having the amino acid sequences or encoded by the nucleic acid sequences of a Genbank data base accession number listed in Table 1 below.

TABLE 1

| SYMBOL | DESCRIPTION | ACCESSION NO. |
|---|---|---|
| APPBPI | Amyloid beta precursor protein binding protein 1, 59 kD | NM_003905 |
| FLJ23251 | hypothetical protein FLJ23251 | NM_024818 |
| GSA7 | ubiquitin activating enzyme E1-like protein | NM_006395 |
| | similar to ubiquitin-activating enzyme E1 (A1S9T and BN75 temperature sensitivity complementing) (*H. sapiens*) | XM_088743 |

TABLE 1-continued

| SYMBOL | DESCRIPTION | ACCESSION NO. |
|---|---|---|
|  | similar to SUMO-1 activating enzyme subunit 1; SUMO-1 activating enzyme E1 N subunit; sentrin/SUMO-activating protein AOS1; ubiquitin-like protein SUMO-1 activating enzyme | XM_090110 |
| SAE1 | SUMO-1 activating enzyme subunit 1 | NM_005500 and XM_009036 |
| UBA2 | SUMO-1 activating enzyme subunit 2 | NM_005499 |
| UBE1 | ubiquitin-activating enzyme E1 (A1S9T and BN75 temperature sensitivity complementing) | NM_003334 and XM_033895 |
| UBE1C | ubiquitin-activating enzyme E1C (UBA3 homolog, yeast) | NM_003968 |
| UBE1L | Ubiquitin-activating enzyme E1-like | NM_003335 |

Further exemplary E1 proteins for use in the invention are disclosed in PCT Publication No. WO 01/75145. Variants of the cited E1 proteins, also included in the term "E1", can be made as described herein.

The invention also contemplates use of variants of a ubiquitin activating agents which retain a characteristic of a native ubiquitin activating agent in being capable of facilitating activation of a ubiquitin conjugating agent. Such ubiquitin activating agent variants generally have an overall amino acid sequence identity of preferably greater than about 75%, more preferably greater than about 80%, even more preferably greater than about 85% and most preferably greater than 90% of the amino acid sequence of a ubiquitin provided above. In some embodiments the sequence identity will be as high as activating agent about 93 to 95 or 98%. Variants of ubiquitin activating agents and other components of the assays of the invention are described below in more detail.

Ubiquitin Conjugating Agents

As used herein "ubiquitin conjugating agent" refers to a ubiquitin agent, usually a protein (e.g., a ubiquitin conjugating enzyme), capable of facilitating transfer or attaching a ubiquitin moiety to a substrate protein through interaction with a ubiquitin ligating agent. In some cases, the ubiquitin conjugating agent is capable of directly transferring or attaching ubiquitin moiety to lysine residues in a target substrate protein. The ubiquitin conjugating agent can be one capable of facilitating transfer or attachment of a ubiquitin moiety to a mono- or poly-ubiquitin moiety, which in turn can be attached to a ubiquitin agent or target protein.

In many embodiments, the ubiquitin conjugating agent is an E2, where the ubiquitin moiety is transferred from E1 to E2, in which the transfer results in a thiolester bond formed between E2 and ubiquitin moiety. In certain embodiments, E2 facilitates transfer or attachment of a ubiquitin moiety to a substrate protein through interaction with an E3 ubiquitin ligating agent, which is defined below.

In the methods and compositions of the present invention, the ubiquitin activating agent can comprise an amino acid sequence or a nucleic acid sequence corresponding to a sequence of an Genbank data base accession number listed in Table 2 below and incorporated herein by reference. Ubiquitin conjugating agents of human cells (indicated by "Hs") are of particular interest.

TABLE 2

| Name | ALIAS | Accession No. (nucleic acid sequences) | Accession No. (amino acid sequences) |
|---|---|---|---|
| UBE2D1 Hs UBC4/5 homolog | UBE2D1, UBCH5A, UBC4/5 homolog | NM_003338.1 | NP_003329.1 |
| UBC9 Gallus gallus | UBC9, SUMO-conjugating enzyme | AB069964.1 | BAB68210.1 |
| UBC9 Mus musculus | mUB69 | U76416.1 | AAB18790.1 |
| UBC9/UBE21 Hs | UBE21 | U45328.1 | AAA86662.1 |
| UBC9 isoform/MGC: 3994 Hs | MGC: 3994, IMAGE: 2819732, UBC9 isoform | BC004437.1 NM_003345.1 | AAH04437.1 NP_003336.1 |
| UBC9 Hs | UBC9, UBE21 |  |  |
| FTS homolog Hs+ laa | fused toes homolog, FLJ13258 | NM_022476.1 | NP_071921.1 |
| FLJ13988 Hs | FLJ13988, clone Y79AA1002027, | AK024050.1 | BAB14800.1 |
| MGC: 13396 Hs | sim to E2-18 | BC010900.1 | AAH10900.1 |
| UBE2V2 Hs | MGC: 13396, IMAGE: 4081461 | NM_003350.2 | NP_003341.1 |
| MGC: 10481 Hs | UBE2V2, EDAF-1, MMS2, UEV2, | BC004862.1 | AAH04862.1 |
| XM_054332.1 Hs | DDVIT1, ED | XM_054332.1 | XP_054332.1 |
| FLJ13855 Hs | MGC: 10481, IMAGE: 3838157 | XM_030444.3 | XP_030444.1 |
| E2-230K homolog Hs |  | NM_022066.1 | NP_071349.1 |
| UBE2V2 Hs | FLJ13855 | NM_003339.1 | NO_003330.1 |
| UBE2D3 Hs 1 SNP | E2-230K ortholog, FLJ12878, | NM_003340.1 | NP_003331.1 |
| Non-canon Ub-conj Enz (NCUBE1) | KIAA1734 | NM_016336.2 | NP_057420.2 |
| HSPC150 Hs | UBE2D2, UBCH5B, UBC4, UBC4/5 homolog | NM_014176.1 | NP_054895.1 |
| Brain 1AP repeat contain 6 (BIRC6) | UBE2D3, UBCH5C, UBC4/5 homolog | NM_016252.1 | NP_057336.1 |

TABLE 2-continued

| Name | ALIAS | Accession No. (nucleic acid sequences) | Accession No. (amino acid sequences) |
|---|---|---|---|
| | NCUBE1, HSU93243, HSPC153, CGI-76 | | |
| | BIRC6, KIAA1289, apollon | | |
| UBC8 *Mus* | E2-20K, UBE2sH | NM_009459.1 | NP_033485.1 |
| UBC8 Hs | UBE2H, UBCH, UBCH2, UBC8 homolog | NM_003344.1 | NP_003335.1 |
| UBC8 Hs 6SNP | | NM-003344.1 | NP-003335.1 |
| UBC8 Hs no 5' | UBE2H, UBCH, UBCH2, UBC8 homolog | | |
| RAD6 homolog Hs | UBE2B, RAD6B, HHR6B, UBC2, RAD6 homolog | NM_003337.1 | NP_003328.1 |
| UBE2V1 var 3 Hs | UBE2V1, CIR1, UEV1, UEV1A, CROC-1, CRO | NM_022442.2 | NP_071887.1 |
| UBE2V1 var 1 Hs early stop, 56aa | | NM_021988.2 | NP_068823.1 |
| UBE2V1 var 2 Hs | UBE2V1, CIR1, UEV1, UEV1A, CROC-1, CRO | NM_003349.3 | NP_003340.1 |
| | UBE2V1, CIR1, UEV1, UEV1A, CROC-1, CRO | | |
| UBE2L6 Hs | UBE2L6, UBCH8, RIG-B | NM_004223.1 | NP_004214.1 |
| UBE2L3 Hs 2 SNP | UBE2L3, UBCH7 | NM_003347.1 | NP_003338.1 |
| UBE2E1 Hs | UBE2E1, UBCH6, UBC4/5 homolog | NM_003341.1 | NP_003332.1 |
| RAD6/UBE2A Hs | UBE2A, RAD6A, HHR6A, UBC2, RAD6 homolog | NM_003336.1 | NP_003327.1 |
| UBE2E3 Hs | | NM_006357.1 | NP_006348.1 |
| UBC12/UBE2M Hs | UBE2E3, UBCH9, UBC4/5 homolog | NM_003969.1 | NP_003960.1 |
| UBC7/UBE2G1 Hs | UBE2M, HUBC12, UBC12 homolog | NM_003342.1 | NP_003333.1 |
| | UBE2G1, UBC7 homolog | | |
| Huntingtin interact prot 2 (HIP2) Hs | HIP2, LIG, E2-25K | NM_005339.2 | NP_005330.1 |
| LIG/HIP2 variant Hs | LIG, HIP2 alternative splicing form | ABO22436.1 | BAA78556.1 |
| UBC6p Hs | UBC6p, UBC6 | NM_058167.1 | NP_477515.1 |
| UBC6 Hs | UBC6 | AF296658.1 | AAK52609.1 |
| HBUCE1/UBE2D2 var Hs | HBUCE1, LOC51619 | NM_015983.1 | NP_057067.1 |
| UBE2G2/UBC7 homolog Hs | UBE2G2, UBC7 homolog | XM_036087.1 | XP_036087.1 |
| NEDD8-conj enzyme 2 (NCE2) Hs | NCE2 | NM_080678.1 | NP_542409.1 |
| CDC34 Hs | CDC34, E2-CDC34, E2-32 complementing | NM_004359.1 | NP_004350.1 |
| IMAGE: 3458173/NICE-5 var | IMAGE: 3458173 | BC000848.1 | AAH00848.1 |
| UBE2C Hs | UBE2C, UBCH10 | NM_007019.1 | NP_008950.1 |
| UBE2C possible short form Hs | UBE2C, UBCH10 | NM_007019.1 | NP_008950.1 |
| UBC3/UBE2N Hs | UBE2N, UBCH-BEN, UBC13 | NM_003348.1 | NP_003339.1 |
| FLJ25157 Hs | hom., sim to bend FLJ25157, highly similar to E2-23 | AK057886.1 | BAB71605.1 |
| TSG101 Hs 1 SNP | Tumor susceptibility gene 101 | NM_006292.1 | NP_006283.1 |
| MGC: 21212/NICE-5 var Hs | MCG: 21212, IMAGE: 3907760, sim to NICE-5 | BC017708.1 | AAH17708.1 |

Hs = *Homo sapiens*;
Mm = *Mus musculus*;

Variants of the above ubiquitin conjugating proteins are suitable for use in the methods and compositions of the present invention. The ubiquitin conjugating agents and variants suitable for use in the methods and compositions of the present invention may be made as described herein.

In exemplary embodiments, the E2 used in the methods and compositions of the present invention comprises an amino acid sequence or nucleic acid sequence of a sequence corresponding to an Genbank data base accession number in the following list: AC37534, P49427, CAA82525, AAA58466, AAC41750, P51669, AAA91460, AAA91461, CAA63538, AAC50633, P27924, AAB36017, Q16763, AAB86433, AAC26141, CAA04156, BAA11675, Q16781, NP_003333, BAB18652, AAH00468, CAC16955, CAB76865, CAB76864, NP_05536, O00762, XP_009804, XP_009488, XP_006823, XP_006343, XP_005934, XP_002869, XP_003400, XP_009365, XP_010361, XP_004699, XP_004019, O14933, P27924, P50550, P52485, P51668, P51669, P49459, P37286, P23567, P56554, and CAB45853, each of which is incorporated herein by reference. Exemplary sequences of interest are those corresponding to Genbank data base accession numbers NP003331, NP003330, NP003329, P49427, AAB53362, NP008950, XP009488 and AAC41750, also incorporated by reference.

In further exemplary embodiments, E2 is one of Ubc5 (Ubch5, e.g., Ubch5c), Ubc3 (Ubch3), Ubc4 (Ubch4) and UbcX (Ubc10, Ubch10). In an exemplary embodiment, E2 is Ubc5c. In an exemplary embodiment, nucleic acids which may be used to make E2 include, but are not limited to, those nucleic acids having sequences disclosed in ATCC accession numbers L2205, 229328, M92670, L40146, U393 17, U393 18, X92962, U58522, S81003, AF031141, AF075599, AJ000519, XM009488, NM007019, U73379, L40146 and D83004, each of which is incorporated herein by reference.

The skilled artisan will appreciate that many different E2 proteins and isozymes are known in the filed and may be used in the present invention, provided that the E2 has ubiquitin conjugating activity. Further exemplary E2 proteins for use in the invention are disclosed in PCT Publication No. WO 01/75145. Also specifically included within the term "E2" are variants of E2, which can be made as described herein.

The invention contemplates use of variants of a ubiquitin conjugating agents which retain a characteristic of a native ubiquitin conjugating agent in being capable of being activated by a ubiquitin activating agent and/or facilitating ubiquitylation of a target substrate protein in connection with a ubiquitin ligating agent. Such ubiquitin conjugating agent variants generally have an overall amino acid sequence identity of preferably greater than about 75%, more preferably greater than about 80%, even more preferably greater than about 85% and most preferably greater than 90% of the amino acid sequence of a ubiquitin conjugating agent provided above. In some embodiments the sequence identity will be as high as about 93 to 95 or 98%. Variants of ubiquitin conjugating agents and other components of the assays of the invention are described below in more detail.

In some embodiments, E2 has a tag, as defined herein, with the complex being referred to herein as "tag-E2". Exemplary E2 tags include, but are not limited to, labels, partners of binding pairs and substrate binding elements. In one embodiment of particular interest, the tag is an affinity tag, e.g., a His-tag or GST-tag.

Variant Polypeptides Differing in Amino Acid Sequence and Fragments

As noted above, the assays of the invention described herein can be conducted with various protein variants including variants of ubiquitin, E1, E2, and poxvirus 28 protein. These variants generally fall into one or more of three classes: substitution, insertion or deletion variants. Variants are generally described as having a sequence similarity (e.g., sequence identity) relative to that of a "reference" sequence, e.g., the sequence of the naturally-occurring protein. It will also be readily appreciated that proteins that share amino acid sequence similarity are encoded by nucleic acids that share nucleotide sequence similarity.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266: 460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "shorter" sequence in the aligned region. The "shorter" sequence is the one having the least actual residues in the aligned region (gaps introduced by WU-Blast-2 to maximize the alignment score are ignored). For example, if one polypeptide is longer than another polypeptide and contains the entire sequence of the shorter sequence, the polypeptides are 100% identical.

The alignment may include the introduction of gaps in the sequences to be aligned. In addition, for sequences which contain either more or fewer amino acids than the reference amino acid sequence, it is understood that in one embodiment, the percentage of sequence identity will be determined based on the number of identical amino acids in relation to the total number of amino acids. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Variants of interest can ordinarily be prepared by site specific mutagenesis of nucleotides in the DNA encoding a protein of the present compositions, using cassette or PCR mutagenesis or other techniques well known in the art, to produce DNA encoding the variant, and thereafter expressing the DNA in recombinant cell culture as outlined above. However, variant protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal desired activity. Techniques for making substitution mutations at predetermined sites in DNA having a known sequence are well known, for example, M13 primer mutagenesis and PCR mutagenesis. Rapid production of many variants may be done using techniques such as the method of gene shuffling, whereby fragments of similar variants of a nucleotide sequence are allowed to recombine to produce new variant combinations. Examples of such techniques are found in U.S. Pat. Nos. 5,605,703; 5,811,238; 5,873,458; 5,830,696; 5,939,250; 5,763,239; 5,965,408; and 5,945,325, each of which is incorporated by reference herein in its entirety. Screening of the mutants is performed using the activity assays of the present invention.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the protein are desired, substitutions of an original residue are generally made in accordance with exemplary substitutions listed below.

Table of Exemplary Amino Acid Substitutions

| Residue | Substituted Residue |
|---------|---------------------|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |

-continued

Table of Exemplary Amino Acid Substitutions

| Residue | Substituted Residue |
|---------|---------------------|
| Met | Leu, Ile |
| Phe | Met, Leu, Tyr |
| Ser | Thr |
| Thr | Ser |
| Trp | Tyr |
| Tyr | Trp, Phe |

Substantial changes in function or immunological identity are made by selecting substitutions that are less conservative than those shown in the above list. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

In one embodiment, the variants typically exhibit the same qualitative biological activity and will elicit the same immune response as the naturally-occurring analogue, although variants also are selected to modify the characteristics of the proteins as needed. Alternatively, the variant may be designed such that the biological activity of the protein is altered. For example, glycosylation sites may be altered or removed.

It will be appreciated that the nucleotide sequences of protein variants can be readily determined, for example based upon the amino acid sequence of the variant and the knowledge of the genetic code. Due to the degeneracy of the genetic code, a nucleotide sequence encoding a protein variant may exhibit a lower sequence identity with the corresponding native nucleotide sequence than the amino acid sequence identity between the variant protein and the native protein. For example, nucleotide sequences share as little as about 66% (i.e., about ⅔) nucleotide sequence identity can encode the same amino acid sequence due to the degeneracy of the genetic code. Thus, nucleic acid encoding a protein variant can have at least 30%, 40%, 50%, 60%, 70%, 80%, 85%, 90%, or 95% sequence identity with a reference nucleic acid, for example, the corresponding nucleic acid encoding the native protein (i.e., the protein prior to modification) from which a variant protein sequence is derived.

The invention also contemplates use of E1, E2 and E3 proteins which are shorter or longer than the corresponding naturally occurring amino acid sequence. That is, portions or fragments of the proteins described herein can be used in the assays of the invention. The fragments of use in the invention retain a biological activity of the protein from which it was derived or with which it share amino acid sequence identity. For example, a ubiquitin fragment useful in the invention is one that can be transferred (or removed from) a substrate protein by the corresponding ubiquitin agents. Similarly, a fragment of a ubiquitin activating agent (e.g., a fragment of E1) of interest is one that retains activity in being modified by a ubiquitin moiety and activating a ubiquitin conjugating agent. A fragment of a ubiquitin conjugating agent (e.g., a fragment of E2) of interest is one that retains activity in interacting with an E3 to facilitate transfer of a ubiquitin moiety to a substrate protein. A ubiquitin ligating agent fragment retains activity in interacting with a target protein and an activated E2 to facilitate transfer of a ubiquitin moiety to the target protein. A target protein fragment of interest is one that can be modified by attachment of and/or removal of ubiquitin moieties by the relevant components of the ubiquitin cascade.

Production of Polypeptides

The subject proteins can be produced according to methods known in the art. In addition, probe or degenerate polymerase chain reaction (PCR) primer sequences may be used to find other related or variant ubiquitin moieties, ubiquitin agents, and target proteins from humans or other organisms.

In one embodiment, the nucleic acids of the invention are part of an expression vector. Using the nucleic acids of the present invention which encode a protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading frame. However, enhancers do not have to be contiguous. Linking is accomplished by ligation at convenient restriction sites. If such sites do not exist, the synthetic oligonucleotide adapters or linkers are used in accordance with conventional practice. The transcriptional and translational regulatory nucleic acid will generally be appropriate to the host cell used to express the protein; for example, transcriptional and translational regulatory nucleic acid sequences from *Bacillus* can be used to express the protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In one embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in one embodiment, the expression vector contains a selectable marker gene to allow the selection of transformed host cells. Selection genes are well known in the art and will vary with the host cell used.

An exemplary expression vector system is a retroviral vector system such as is generally described in PCT/US97/01019 and PCT/US97/01048, both of which are hereby expressly incorporated by reference. Constructs also are described in U.S. Pat. No. 6,153,380, which is expressly incorporated herein by reference.

Proteins of the present invention are produced by culturing a host cell transformed with an expression vector containing nucleic acid encoding the protein, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction.

Appropriate host cells include yeast, bacteria, archaebacteria, fungi, and insect and animal cells, including mammalian cells. Of particular interest are *Drosophila melanogaster* cells, *Pichia pastoris* and *P. methanolica*, *Saccharomyces cerevisiae* and other yeasts, *E. coli*, *Bacillus subtilis*, SF9 cells, SF21 cells, C129 cells, Saos-2 cells, Hi-5 cells, 293 cells, *Neurospora*, BHK, CHO, COS, and HeLa cells. Of greatest interest are A549, HeLa, HUVEC, Jurkat, BJAB, CHMC, primary T cells and macrophage.

In a one embodiment, the proteins are expressed in mammalian cells, especially human cells. Mammalian expression systems are also known in the art, and include retroviral systems. A mammalian promoter (i.e., a promoter functional in a mammalian cell) is any DNA sequence capable of binding mammalian RNA polymerase and initiating the downstream (3') transcription of a coding sequence for a protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter can also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Where the host cell is a bacterial cell, a suitable bacterial promoter is any nucleic acid sequence capable of binding bacterial RNA polymerase and initiating the downstream (3') transcription of the coding sequence of a protein into mRNA. A bacterial promoter has a transcription initiation region which is usually placed proximal to the 5' end of the coding sequence. This transcription initiation region typically includes an RNA polymerase binding site and a transcription initiation site. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

The protein may also be made as a fusion protein, using techniques well known in the art. Thus, for example, the protein may be made fusion nucleic acid encoding the peptide or may be linked to other nucleic acid for expression purposes. Similarly, proteins of the invention can be linked to tags that are protein labels, such as green fluorescent protein (GFP), red fluorescent protein (RFP), blue fluorescent protein (BFP), yellow fluorescent protein (YFP), etc. The fusions may include other constructs as well, including separation sites such as 2a site and internal ribosomal entry sites IRES, which are particularly useful in the construct as IRES-label to provide a method of tracking infected cells.

Expression vectors for bacteria are well known in the art, and include vectors for *Bacillus subtilis*, *E. coli*, *Streptococcus cremoris*, and *Streptococcus lividans*, among others. The bacterial expression vectors are transformed into bacterial host cells using techniques well known in the art, such as calcium chloride treatment, electroporation, and others. In one embodiment, proteins are produced in insect cells. Expression vectors for the transformation of insect cells, and in particular, baculovirus-based expression vectors, are well known in the art. In another embodiment, proteins are produced in yeast cells. Yeast expression systems are well known in the art, and include expression vectors for *Saccharomyces cerevisiae*, *Candida albicans* and *C. maltosa*, *Hansenula polymorpha*, *Kluyveromyces fragilis* and *K. lactis*, *Pichia guillerimondii* *P. methanolica* and *P. pastoris*, *Schizosaccharomyces pombe*, and *Yarrowia lipolytica*. Promoter sequences for expression in yeast include the inducible GAL 1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TW1, and ALG7, which confers resistance to tunicamycin; the neomycin phosphotransferase gene, which confers resistance to G4 18; and the CUP 1 gene, which allows yeast to grow in the presence of copper ions.

Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the ubiquitin protein may be purified using a standard anti-ubiquitin antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the protein. In some instances no purification will be necessary.

Expression of p28 in bacterial cells is described by Senkevich et al, (J. Virology 69: 4103–4111, 1995).

Covalently Modified Proteins, Including Detectably Labeled Ubiquitin Agents

In one embodiment, covalent modifications of polypeptides are included within the scope of this invention. Such covalent modifications generally find use in in vitro assays as described in more detail in U.S. Ser. No. 09/800,770, filed Mar. 6, 2001, which is expressly incorporated herein by reference.

Tagged Polypeptides

The subject polypeptides can be modified so that they comprise a tag. By "tag" is meant an attached molecule or molecules useful for the identification or isolation of the attached molecule(s), which can be substrate binding molecules. For example, a tag can be an attachment tag or a label tag. Components having a tag are referred to as "tag-X", wherein X is the component. For example, a ubiquitin moiety comprising a tag is referred to herein as "tag-ubiquitin moiety". Preferably, the tag is covalently bound to the attached component.

When more than one component of a combination has a tag, the tags will be numbered for identification, for example "tag1-ubiquitin moiety". Components may comprise more than one tag, in which case each tag will be numbered, for example "tag 1,2-ubiquitin moiety". Exemplary tags include, but are not limited to, a label, a partner of a binding pair, and a surface substrate binding molecule (or attachment tag). As will be evident to the skilled artisan, many molecules may find use as more than one type of tag, depending upon how the tag is used. In one embodiment, the tag or label as described below is incorporated into the polypeptide as a fusion protein.

As will be appreciated by those in the art, tagcomponents of the invention can be made in various ways, depending largely upon the form of the tag. Components of the invention and tags are preferably attached by a covalent bond. Examples of tags are described below.

Exemplary Tags Useful in the Invention

As noted above, "tags" can be any of a variety of labels, which can be detected either directly or indirectly. Tagged ubiquitylation cascade proteins, tagged substrate proteins, and tagged retroviral ubiquitylation modulator protein find particular use in the screening assays of the invention, described below in more detail.

By "label" or "detectable label" is meant a molecule that can be directly (i.e., a primary label) or indirectly (i.e., a secondary label) detected; for example a label can be visualized and/or measured or otherwise identified so that its presence or absence can be known. As will be appreciated by those in the art, the manner in which this is performed will depend on the label. Exemplary labels include, but are not limited to, fluorescent labels (e.g. GFP) and label enzymes.

In one embodiment, the tag is a polypeptide which is provided as a portion of a chimeric molecules comprising a first polypeptide fused to another, heterologous polypeptide or amino acid sequence. In one embodiment, such a chimeric molecule comprises a fusion of a first polypeptide (e.g., a ubiquitin moiety, ubiquitin agent, or target protein) with a tag polypeptide. The tag is generally placed at the amino-or carboxyl-terminus of the polypeptide. The tag polypeptide can be, for example, a polypeptide which provides an epitope to which an anti-tag antibody can selectively bind, a polypeptide which serves as a ligand for binding to a receptor (e.g., to facilitate immobilization of the chimeric molecule on a substrate); an enzyme label (e.g., as described further below); or a fluorescent label (e.g., as described further below). Tag polypeptides provide for, for example, detection using an antibody against the tag polypeptide, and/or a ready means of isolating or purifying the tagged polypeptide (e.g., by affinity purification using an anti-tag antibody or another type of receptor-ligand matrix that binds to the tag). In an alternative embodiment, the chimeric molecule may comprise a fusion of a polypeptide disclosed herein with an immunoglobulin or a particular region of an immunoglobulin. For a bivalent form of the chimeric molecule, such a fusion could be to the Fc region of an IgG molecule. Tags for components of the invention are defined and described in detail below.

The production of tag-polypeptides by recombinant means is within the knowledge and skill in the art. Production of FLAG-labeled proteins is well known in the art and kits for such production are commercially available (for example, from Kodak and Sigma). Methods for the production and use of FLAG-labeled proteins are found, for example, in Winston et al., Genes and Devel. 13:270–283 (1999), incorporated herein in its entirety, as well as product handbooks provided with the above-mentioned kits.

Production of proteins having His-tags by recombinant means is well known, and kits for producing such proteins are commercially available. Such a kit and its use is described in the QIAexpress Handbook from Qiagen by Joanne Crowe et al., hereby expressly incorporated by reference.

By "fluorescent label" is meant any molecule that may be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Bluer™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference.

Suitable fluorescent labels include, but are not limited to, green fluorescent protein (GFP; Chalfie, et al., Science 263(5148):802–805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, $8^{th}$ Floor, Montreal (Quebec) Canada H3H 1J9; 2. Stauber, R. H. Biotechniques 24(3):462–471 (1998); 3. Heim, R. and Tsien, R. Y. Curr. Biol. 6:178–182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408–5417 (1993)), $-galactosidase (Nolan, et al., Proc Natl Acad Sci USA 85(8):2603–2607 (April 1988)) and *Renilla* WO 92/15673; WO 95/07463; WO 98/14605; WO 98/26277; WO 99/49019; U.S. Pat. Nos. 5,292,658; 5,418, 155; 5,683,888; 5,741,668; 5,777,079; 5,804,387; 5,874, 304; 5,876,995; and 5,925,558), and Ptilosarcus green fluorescent proteins (pGFP) (see WO 99/49019). All of the above-cited references are expressly incorporated herein by reference.

In some instances, multiple fluorescent labels are employed. In one embodiment, at least two fluorescent labels are used which are members of a fluorescence resonance energy transfer (FRET) pair. FRET can be used to detect association/dissociation of, for example, a ubiquitin ligating agent (e.g., an E3) and a target substrate protein; a ubiquitin conjugating agent (e.g., an E2) and a target substrate protein; a ubiquitin ligating agent (e.g., an E3) and a ubiquitin conjugating agent (e.g., an E2); and the like.

FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Forster radius, which is typically 10–100 angstroms. Changes in the fluorescence emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity.

Binding of such molecules will result in an increased fluorescence emission of the acceptor and/or quenching of the fluorescence 15 emission of the donor. FRET pairs (donor/acceptor) useful in the invention include, but are not limited to, EDANS/fluorescien, IAEDANS/fluorescein, fluoresceidtetramethylrhodamhe, fluoresceidLC Red 640, fluoresceidcy 5, fluoresceidCy 5.5 and fluoresceidLC Red.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, DABCYL, QSY 7 and QSY 33. Useful fluorescent donodquencher pairs include, but are not limited to EDANS/DABCYL, Texas RedLDABCYL, BODIPYDABCYL, Lucifer yellowDABCYL, coumarin/DABCYL and fluoresceidQSY 7 dye.

The skilled artisan will appreciate that FRET and fluorescence quenching allow for monitoring of binding of labeled molecules over time, providing continuous information regarding the time course of binding reactions. It is important to remember that ubiquitin is ligated to substrate protein by its terminal carboxyl group to a lysine residue, including lysine residues on other ubiquitin. Therefore, attachment of labels or other tags should not interfere with either of these active groups on the ubiquitin Amino acids may be added to the sequence of protein, through means well known in the art and described herein, for the express purpose of providing a point of attachment for a label. In one embodiment, one or more amino acids are added to the sequence of a component for attaching a tag thereto, with a fluorescent label being of particular interest. In one embodiment, the amino acid to which a fluorescent label is attached is Cysteine.

By "label enzyme" is meant an enzyme which may be reacted in the presence of a label enzyme substrate which produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., *Previews* 247:6–9 (1998), Young, *J. Virol. Methods* 24:227–236 (1989), which are each hereby incorporated by reference in their entirety.

By "radioisotope" is meant any radioactive molecule. Suitable radioisotopes for use in the invention include, but are not limited to 14C, 3H, 32P, 33P, 35S, 125I, and 131I. The use of radioisotopes as labels is well known in the art.

In addition, labels may be indirectly detected, that is, the tag is a partner of a binding pair. By "partner of a binding pair" is meant one of a first and a second moiety, wherein said first and said second moiety have a specific binding affinity for each other. Suitable binding pairs for use in the invention include, but are not limited to, antigendantibodies (for example, digoxigeninlanti-digoxigenin, dinitrophenyl (DNP)/anti-DNP, dansyl-X-anti-dansyl, Fluoresceidantifluorescein, Lucifer yellow/anti-lucifer yellow, and rhodamine anti-rhodamine), biotirdavid (or biotirdstreptavidin) and calmodulin binding protein (CBP)/calmodulin. Other suitable binding pairs include polypeptides such as the FLAG-peptide (Hopp et al., BioTechnol, 6:1204–1210 (1988)); the KT3 epitope peptide (Martin et al., Science, 255:192–194 (1992)); tubulin epitope peptide (Skinner et al., J. Biol. Chem., 266: 15 163–15 166 (1991)); and the T7 gene 10 protein peptide tag (Lutz-Freyemuth et al., Proc. Natl. Acad. Sci. USA, a:6393–6397 (1990)) and the antibodies each thereto. Generally, in one embodiment, the smaller of the binding pair partners serves as the tag, as steric considerations in ubiquitin ligation may be important. As will be appreciated by those in the art, binding pair partners may be used in applications other than for labeling, such as immobilization of the protein on a substrate and other uses as described below.

As will be appreciated by those in the art, a partner of one binding pair may also be a partner of another binding pair. For example, an antigen (first moiety) may bind to a first antibody (second moiety) which may, in turn, be an antigen for a second antibody (third moiety). It will be further appreciated that such a circumstance allows indirect binding of a first moiety and a third moiety via an intermediary second moiety that is a binding pair partner to each. As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

In one embodiment, the tag is surface substrate binding molecule. By "surface substrate binding molecule" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate (Field et al., Mol. Cell. Biol., 8:2159–2165 (1988)); the c-myc tag and the 8F9,3C7,6E107 G4, B7 and 9E10 antibody substrates thereto (Evan et al., Molecular and Cellular Biol, 5:3610–3616 (1985)]; and the Herpes Simplex virus glycoprotein D (gD) tag and its antibody substrate (Paborsky et al., Protein Engineering, 3(6):547–553 (1990)). In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin et al., Bioconj, Chem. 2:342–348 (1991); Torchilin et al., supra; Trubetskoy et al., Bioconi. Chem. 33323–327 (1992); King et al., Cancer Res. 54:6176–6185 (1994); and Wilbur et al., Bioconjugate Chem. 5:220–235 (1994) (all of which are hereby expressly incorporated by reference), and attachment of or production of proteins with antigens is described above. Calmodulin-embedded substrates are commercially available, and production of proteins with CBP is described in Simcox et al., Strategies 8:40–43 (1995), which is hereby incorporated by reference in its entirety.

Where appropriate, functionalization of labels with chemically reactive groups such as thiols, amines, carboxyls, etc. is generally known in the art. In one embodiment, the tag is functionalized to facilitate covalent attachment.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, $6^{th}$ Ed. 1996, hereby incorporated by reference. A biotinylated substrate can be attached to a biotinylated component via avidin or streptavidin. Similarly, a large number of haptenylation reagents are also known. Methods for labeling of proteins with radioisotopes are known in the art. For example, such methods are found in Ohta et al., Molec. Cell 3:535–541 (1999), which is hereby incorporated by reference in its entirety.

The covalent attachment of the tag may be either direct or via a linker. In one embodiment, the linker is a relatively short coupling moiety, that is used to attach the molecules. A coupling moiety may be synthesized directly onto a component of the invention, ubiquitin for example, and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer.

In one embodiment, the covalent attachment is direct, that is, no linker is used. In this embodiment, the component can contain a functional group such as a carboxylic acid which is used for direct attachment to the functionalized tag. It should be understood that the component and tag may be attached in a variety of ways, including those listed above. What is important is that manner of attachment does not significantly alter the functionality of the component. For example, in tag-ubiquitin, the tag should be attached in such a manner as to allow the ubiquitin to be covalently bound to other ubiquitin to form polyubiquitin chains.

As will be appreciated by those in the art, the above description of covalent attachment of a label and ubiquitin applies equally to the attachment of virtually any two molecules of the present disclosure. In one embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag 32 will depend on the site of attachment to either a linker, as outlined above or a component of the invention. Thus, for example, for direct linkage to a carboxylic acid group of a ubiquitin, amino modified or hydrazine modified tags will be used for coupling via carbodiimide chemistry, for example using 1-ethyl-3-(3-dimethylaminopropyl)-carbodiimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

In one embodiment, ubiquitin moiety is in the form of tag-ubiquitin moiety, wherein, tag is a partner of a binding pair. In one example is the tag is FLAG and the binding partner is anti-FLAG. In this embodiment, a label is attached to the FLAG by indirect labeling. In another embodiment, the label is a label enzyme, which can be, for example, horseradish peroxidase, which is reacted with a fluorescent label enzyme substrate. In one embodiment, the label enzyme substrate is Luminol. Alternatively, the label is a fluorescent label.

In another embodiment, the ubiquitin moiety is in the form of tag-ubiquitin moiety, wherein the tag is a fluorescent label. In one embodiment of interest, the ubiquitin moiety is in the form of tag1-ubiquitin and tag2-ubiquitin, wherein tag1 and tag2 are the members of a FRET pair. In an alternate embodiment, the ubiquitin moiety is in the form of tag1-ubiquitin and tag2-ubiquitin, wherein tag1 is a fluorescent label and tag2 is a quencher of the fluorescent label. In a related embodiment, when the tags ubiquitin and tag2-ubiquitin moieties are bound through the activity of a ubiquitin ligase, the tag1 and tag2 are within about 100, 70, 50, 40, or 30 or less angstroms of each other.

In another embodiment, ubiquitin is in the form of tag1, 2-ubiquitin and tag1,3-ubiquitin, wherein tag1 is a member of a binding pair, e.g., FLAG, tag2 is a fluorescent label and tag3 is either a fluorescent label such that tag2 and tag3 are members of a FRET pair or tag3 is a quencher of tag2. In one embodiment, one or more amino acids are added to the ubiquitin sequence, using recombinant techniques as described herein, to provide an attachment point for a tag, e.g., a fluorescent label or a quencher. In one embodiment, the one or more amino acids are Cys or Ala-Cys. Preferably, the one or more amino acids are attached to the N-terminal of the ubiquitin. In one exemplary embodiment, the one or more amino acids intervenes the sequence of a FLAG tag and the ubiquitin. In an exemplary embodiment, the tag, e.g., a fluorescent label or a quencher, is attached to the added Cysteine.

Glycosylation Variants and Other Variants

Another type of covalent modification of a polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide, and/or adding one or more glycosylation sites that are not present in the native sequence polypeptide.

Addition of glycosylation sites to polypeptides may be accomplished by altering the amino acid sequence thereof. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at pre-selected bases such that codons are generated that will translate into the desired amino acids.

Alternatively, the variant may be designed such that the biological activity of the protein is altered. For example, glycosylation sites may be altered or removed. Covalent modifications of polypeptides are included within the scope of this invention. One type of covalent modification includes reacting targeted amino acid residues of a polypeptide with an organic derivatizing agent that is capable of reacting with selected side chains or the N-or C-terminal residues of a polypeptide. Derivatization with bifunctional agents is useful, for instance, for crosslinking a protein to a water-insoluble support matrix or surface for use in the method for screening assays, as is more fully described below. Commonly used crosslinking agents include, e.g., 1,1-bis(diazoacetyl)-2-phenylethane, glutaraldehyde, -hydroxy-succinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1, % octane and agents such as methyl-3-[(p-azidophenyl)dithio] propioimidate. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains (Creighton, Proteins: Structure and Molecular Properties, W.H. Freeman & Co., San Francisco, pp. 79–86 (1983)), acetylation of the N-terminal amine, and amidation of any C-terminal carboxyl group.

Further means of increasing the number of carbohydrate moieties on a polypeptide is by chemical or enzymatic coupling of glycosides to the polypeptide. Such methods are described in the art, e.g., in WO 87/05330, and in Aplin and Wriston, CRC Crit. Rev. Biochem., pp. 259–306 (1981). Removal of carbohydrate moieties present on the polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 25952 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzynol., 138:350 (1987). Another type of covalent modification of a protein comprises linking the polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Candidate Agents

The assays of the invention are designed to identify candidate agents that modulate the ubiquitin ligase activity of a poxvirus p28 protein. By "modulate" is meant a compound which can facilitate an increase or decrease ubiquitylation, with agents that decrease ubiquitylation being of particular interest.

By "candidate", "candidate agent", "candidate modulator", "candidate ubiquitylation modulator" or grammatical equivalents herein, which terms are used interchangeable herein, is meant any molecule, e.g. proteins (which herein includes proteins, polypeptides, and peptides), small (i.e., 5–1000 Da, 100–750 Da, 200–500 Da, or less than 500 Da in size), or organic or inorganic molecules, polysaccharides, polynucleotides, etc. which are to be tested for ubiquitination modulator activity. Candidate agents encompass numerous chemical classes. In one embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, usually at least two of the functional chemical groups. The candidate agents often comprise cyclical carbon or heterocyclic structures and or aromatic or polyaromatic structures substituted with one or more chemical functional groups.

Candidate modulators are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In one embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate modulator prior to the assay; only candidate modulators that affect ubiquitylation of a target substrate protein of interest need be identified.

In another embodiment, the candidate modulators are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In one embodiment, candidate modulators include proteins, nucleic acids, and chemical moieties. In one embodiment, the candidate modulators are naturally occurring proteins or fragments of naturally occurring proteins. Thus, for example, cellular extracts containing proteins, or random or directed digests of proteinaceous cellular extracts, may be tested, as is more fully described below. In this way libraries of procaryotic and eucaryotic proteins may be made for screening against any number of ubiquitin ligase compositions. Other embodiments include libraries of bacterial, fungal, viral, and mammalian proteins, with the latter being preferred, and human proteins being especially preferred.

In one embodiment, the candidate modulators are peptides of from about 2 to about 50 amino acids, with from about 5 to about 30 amino acids being usual, and from about 8 to about 20 being particularly of interest. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position.

The synthetic process can be designed to generate randomized proteins or nucleic acids, to allow the formation of all or most of the possible combinations over the length of the sequence, thus forming a library of randomized candidate bioactive proteinaceous agents. A library of all combinations of a peptide 7 to 20 amino acids in length has the potential to code for $20^7$ to $20^{20}$ different peptides. Thus, with libraries of $10^7$ to $10^8$ different molecules the present methods allow a "working" subset of a theoretically complete interaction library for 7 amino acids, and a subset of shapes for the $20^{20}$ peptide library. Thus, in one embodiment, at least $10^6$, $10^7$, or $10^8$. Maximizing library size and diversity is of interest.

In one embodiment, the library is fully randomized, with no sequence preferences or constants at any position. In one embodiment, the library is biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

A number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc.

As described above generally for proteins, nucleic acid candidate modulator may be naturally occurring nucleic acids, random nucleic acids, or "biased" random nucleic acids. For example, digests of genomes may be used as is outlined above for proteins. Where the ultimate expression product is a nucleic acid, at least 10, at least 12, more usually at least 15, normally at least 21 nucleotide positions need to be randomized, with more preferable if the randomization is less than perfect. Similarly, at least 5, at least 6, more usually at least 7 amino acid positions need to be randomized; again, more are preferable if the randomization is less than perfect.

In one embodiment, the candidate modulators are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention. Exemplary molecules for use in the subject assays may be found in: "Rhodanine Compositions for use as Antiviral Agents", Ser. No. 60/514,951 filed on Oct. 28, 2003; U.S. provisional patent application Ser. No. 60/509,780; and US provisional patent application entitled "Ubiquitin Ligase Inhibitors", Ser. No. 60/514,951 filed on $9^{th}$ Oct. 2003, which applications are incorporated herein by reference in their entirety.

Assay Formats

The invention provides methods for assessing the effect of a candidate agent upon the ubiquitin ligase activity of a poxvirus p28 protein. In these assays, the influence of candidate agent on the ubiquitin ligase activity of a poxvirus p28 protein can be observed and assessed.

In general, the assays of the invention are carried out by bringing into contact various ubiquitylation agents, including a poxvirus p28 protein, and assessing the effect of the candidate agent upon substrate protein ubiquitylation.

Identification of Agents that Decrease Ubiquitylation

In one embodiment, the method involves combining (e.g., in a test sample) a candidate agent, ubiquitin, a ubiquitin activating agent, a ubiquitin conjugating agent, and a poxvirus p28 protein under conditions suitable for ubiquitylation of a substrate polypeptide, e.g., the poxvirus p28 protein. The level of ubiquitylated substrate polypeptide is assessed either qualitatively or quantitatively. A decrease in ubiquitylated substrate polypeptide in the presence of the candidate agent relative to a level in the absence of the candidate agent indicates the agent causes a decrease in ubiquitylation of the substrate protein by p28.

As would be apparent to one of skill in the art, these assays may be performed in conjunction with suitable controls, which controls may include an E3 protein that is not a poxvirus p28 protein, assays that do not contain a candidate agent, and the like, to determine whether an agent specifically acts on the ubiquitin ligase activity of poxvirus p28 protein, or some other aspect of ubiquitylation.

An agent that reduces ubiquitylation by reducing the ligase activity of poxvirus p28 protein finds use as a therapeutic agent for treatment of poxvirus infections. In most embodiments, an agent that reduces poxvirus p28 protein ligase activity will decrease activity (and thereby decrease the amount of ubiquitylation) by greater than about 20%, greater than about 40%, greater then about 60%, greater than about 80%, greater than about 90%, greater than about 95%, or greater than about 98%, or more, as compared to controls that do not contain the agent. In many embodiments, agents that have an $IC_{50}$ (the $IC_{50}$ is the concentration of agent that reduces activity by 50%, as compared to controls in the absence of an agent) of about 500 nM or less, about 100 nM or less, about 50 nM or less, about 10 nM or less, about 5 nM or less, or about 1 nM or less, are of especial interest as therapeutic agents for poxvirus infection.

In related embodiments, the assay uses a tagged ubiquitin moiety (tag-Ub), which can be tagged as discussed above.

Cell-Free Screening Assays

In general, the subject method involves combining at least a minimum number of required ubiquitin agents, e.g., ubiquitin, an E1, an E2 and a poxvirus p28 protein, and assessing either qualitatively or quantitatively a level of ubiquitylation activity. Ubiquitylation can be assessed by detection of mono-ubiquitylation, poly-ubiquitylation, or both, and can be assessed by detection of auto-ubiquitylation of p28 polypeptide.

Assessing ubiquitylation activity can be accomplished in a variety of ways. In general, the assay methods involve combining ubiquitin agents and with other components, such as a candidate agent. By "combining" is meant the addition of the various components into a receptacle under conditions in which ubiquitylation of a substrate may take place.

In one embodiment, the receptacle is a well of a 96 well plate or other commercially available multiwell plate. In another embodiment, the receptacle is the reaction vessel of a FACS machine. Other receptacles useful in the present invention include, but are not limited to 384 well plates and 1536 well plates. Still other receptacles useful in the present invention will be apparent to the skilled artisan.

The addition of the components may be sequential or in a predetermined order or grouping, as long as the conditions amenable to ubiquitin ligase activity are obtained. Such conditions are well known in the art, and optimization of such conditions is routine in the art.

The components of the present compositions may be combined in varying amounts. In one embodiment, ubiquitin is combined at a final concentration of 5 ng to 200 ng per 100 μl reaction solution, preferably at about 100 ng per 100 μl reaction solution. For example, a ubiquitin activating agent (e.g, E1) can be combined at a final concentration of from 1 to 50 ng per 100 μl reaction solution, more preferably from 1 ng to 20 ng per 100 μl reaction solution, most preferably from 5 ng to 10 ng per 100 μl reaction solution. In another example, a ubiquitin conjugating agent (e.g., E2) is combined at a final concentration of 10 to 100 ng per 100 μl reaction solution, more preferably 10–50 ng per 100 μl reaction solution. In another example, a poxvirus p28 protein is combined at a final concentration of from 1 ng to 500 ng per 100 μl reaction solution, more preferably from 50 to 400 ng per 100 μl reaction solution, still more preferably from 100 to 300 ng per 100 μl reaction solution, most preferably about 100 ng per 100 μl reaction solution.

The components of the invention are combined under reaction conditions that favor ubiquitylation activity (e.g., ubiquitin ligase activity of p28 polypeptide). Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.5 and 1.5 hours will be sufficient.

A variety of other reagents may be included in the compositions. These include reagents like salts, solvents, buffers, neutral proteins, e.g. albumin, detergents, etc. which may be used to facilitate optimal ubiquitylation enzyme activity and/or reduce non-specific or background interactions. Also reagents that otherwise improve the efficiency of the assay, such as protease inhibitors, nuclease inhibitors, anti-microbial agents, etc., may be used. The compositions can also include adenosine tri-phosphate (ATP).

The mixture of components may be added in any order that promotes ubiquitylation or de-ubiquitylation as appropriate, or optimizes identification of candidate modulator effects. In one embodiment, ubiquitin is provided in a reaction buffer solution, followed by addition of the ubiquitylation enzymes. In an alternate embodiment, ubiquitin is provided in a reaction buffer solution, a candidate modulator is then added, followed by addition of the ubiquitylation enzymes.

In one example, at least one of the components is immobilized on a substrate, e.g., the poxvirus p28 protein. Binding of assay components may be done directly or indirectly (e.g., via covalent or non-covalent binding to a component which is bound to the substrate). Binding of the component can be via a tag moiety, which may or may not provide a detectable signal. In another embodiment, ubiquitin conjugating agent (e.g., E2) is bound to a surface substrate. In general, any substrate binding molecule can be used.

As will be appreciated by those of skill in the art, the surface substrate binding element and substrate to which the element binds can be selected according to the design of the assay and the desired characteristics, e.g., an element-substrate combination that will be effective for facilitating the separation of bound and unbound ubiquitin. The substrate used in embodiments involving immobilization of an assay component can be any suitable substrate, e.g., a well of a multi-well plate, a bead, and the like.

In another embodiment, the ubiquitin agents and other assay components are free in solution. In this embodiment, ubiquitylation activity can be monitored using a system that produces a signal which varies with the extent of ubiquitylation, such as the fluorescence resonance energy transfer (FRET) system described in detail below. In one embodiment, the ubiquitin is labeled, either directly or indirectly, as further described below, and the amount of label is measured. This allows for easy and rapid detection and measurement of ligated ubiquitin, making the assay useful for high-throughput screening applications. In one embodiment, the signal of the label varies with the extent of ubiquitylation, such as in the FRET system described below. One of ordinary skill in the art will recognize the applicability of the present invention to screening for agents which modulate ubiquitylation.

In a related embodiment, the assay composition comprises tag1-ubiquitin, tag2-ubiquitin, E1, E2 and poxvirus p28. In one embodiment, tag1 and tag2 are labels, preferably fluorescent labels, most preferably tag1 and tag2 are a FRET pair. In this embodiment, ubiquitylation is measured by measuring the fluorescent emission spectrum. This measuring may be continuous or at one or more times following the combination of the components. Alteration in the fluorescent emission spectrum of the combination as compared with unligated ubiquitin indicates the amount of ubiquitylation. The skilled artisan will appreciate that in this embodiment, alteration in the fluorescent emission spectrum results from ubiquitin bearing different members of the FRET pair being brought into close proximity, either through the formation of polyubiquitin and/or by binding nearby locations on a protein, preferably a target protein Detection of Ubiquitylation Once combined, the level of ubiquitylation can be assessed in a variety of ways. For example, the level of ubiquitylated substrate protein and/or the degree of ubiquitylation of the substrate protein can be assessed; the level of free ubiquitin can be assessed; the association of substrate protein with a ubiquitin conjugating agent; association of a substrate protein, ubiquitin conjugating agent, and ubiquitin ligating agent; and other variations that will be readily appreciated by the ordinarily skilled artisan. As will also be apparent to the skilled artisan, the detection of ubiquitin bound will encompass not only the particular ubiquitin bound directly to the corresponding protein (e.g., ubiquitin activating agent, ubiquitin conjugating agent, ubiquitin ligating agent, and/or substrate protein), but also the ubiquitin proteins bound in a polyubiquitin chain. In one embodiment, the assay is conducting by assessing ubiquitin ligase activity as described in PCT Publication No. WO 01/75145, which application is incorporated by reference herein in its entirety.

In one embodiment, ubiquitylation is measured, which can be accomplished by, for example, detection of a tag attached to the ubiquitin moiety, e.g., a fluorescent label. In another embodiment, the tag attached to the ubiquitin moiety is an enzyme label or a binding pair member which is indirectly labeled with an enzyme label. In this latter embodiment, the enzyme label substrate produces a fluorescent reaction product. In either of these embodiments, the amount of ubiquitin bound is measured by luminescence. As used herein, "luminescence" or "fluorescent emission" means photon emission from a fluorescent label. In an embodiment where FRET pairs are used, fluorescence measurements may be taken continuously or at time-points during the ligation reaction. Equipment for such measurement is commercially available and easily used by one of ordinary skill in the art to make such a measurement.

Other modes of measuring bound ubiquitin are well known in the art and easily identified by the skilled artisan for each of the labels described herein. For instance, radio-isotope labeling may be measured by scintillation counting, or by densitometry after exposure to a photographic emulsion, or by using a device such as a PhosphorImager. Likewise, densitometry may be used to measure bound ubiquitin following a reaction with an enzyme label substrate that produces an opaque product when an enzyme label is used.

In one embodiment, the assay is conducted to detect ubiquitin ligase activity. In this embodiment, the assay can be performed by adapting the assays described in PCT Publication No. WO 01/75145, which describes assay for detecting ubiquitin ligase activity, including such assays conducted in a cell-free environment.

As well as identifying agents that may be used as antiviral agents, the subject assays may be modified to identify targets for the treatment of poxvirus infection. In general, the methods involve contacting a poxvirus p28 protein with a candidate cellular polypeptide in the presence of ubiquitin, (and usually an E1 and an E2 protein), and determining if the candidate cellular polypeptide is ubiquitylated by the p28 polypeptide. In such assays, for example, a cDNA library may be used to produce a plurality of cellular proteins in a corresponding plurality of cells in which a ubiquitin, a poxvirus p28, an E1 protein and an E2 protein are also produced. The cells, or lysates thereof, may be assayed to determine if the protein encoded by the cDNA is ubiquitylated. If the protein encoded by the cDNA is ubiquitylated, the cDNA may be sequenced and the identify of the encoded protein, i.e., the cellular target for poxvirus p28, can become known.

Cell-Based Assays

In one embodiment, the assay is conducted in a cell, usually a mammalian cell. In some embodiments, the assays are carried out in cells that are susceptible to poxvirus infection and/or permissive to poxvirus replication. In another embodiment, the cell is a mammalian cell that constitutively or inducibly expresses a poxvirus p28 polypeptide from a recombinant construct which may be either extrachromosomal or chromosomally integrated.

In general, in this embodiment the ubiquitin agents, are provided in a host cell, e.g., by expression of an endogenous or exogenous nucleic acid encoding the polypeptides, or by introduction of the polypeptides by, e.g., viral delivery.

Where co-expression of assay components is desired, co-expression may be achieved by introducing into the cell a vector comprising nucleic acids encoding two or more of the assay components, or by introduction of separate vectors, each comprising a single component of the desired assay components. In one embodiment, the candidate agents are peptides, e.g., randomized peptides, which can also be expressed in the host cell.

In general, the host cells used in cell-based assays of the invention mammalian cells, particularly human cells. Where mammalian cells are used, essentially any mammalian cells can be used, with mouse, rat, primate and human cells being particularly preferred.

The ordinarily skilled artisan will appreciate that various assay designs with respect to the assay component and to the methods of detection of ubiquitylation activity described above can be readily adapted for implementation in a cell-based assay.

In one embodiment, the assay is conducted by assessing ubiquitin ligase activity as described in PCT Publication No. WO 01/75145, which application is incorporated by reference herein in its entirety. Further methods for assessing ubiquitylation activity (e.g., using functional assays) are described in U.S. application serial no. U.S. Ser. No. 10/232,951, filed Aug. 30, 2002, and in PCT application serial no. PCT/US03/026843, filed Aug. 29, 2003, each of which applications is incorporated herein by reference in its entirety.

In general, cell-based assays involve contacting a cell containing the assay components with a candidate agent, and culturing the cell for a suitable period and under suitable conditions to allow for ubiquitylation to occur with respect to the substrate protein. The ordinarily skilled artisan will appreciate that precise culture methods will vary according to, for example, the host cell used, and is susceptible to ready optimization. Methods and means for detecting ubiquitylation activity can be adapted from those described above for cell-free assays.

In one embodiment, the assay is designed so as to be readily amenable for use in high-throughput assays. Preferably, in this embodiment, ubiquitylation activity can be detected without the need for isolation of, for example, ubiquitylated substrate protein or lysis of the host cell. For example, the FRET embodiment can be employed so that a level of ubiquitylation activity can be readily associated with a detectable signal that can be extrapolated to a level of ubiquitylation activity. For example, the intensity of the detectable signal can be associated with a level of ubiquitylation activity in the cell.

The cells can be cultured in any suitable receptacle, preferably in a receptacle that is amenable for high throughput assays (e.g., a multi-well plate).

High-Throughput Assays

In one embodiment, multiple assays are performed simultaneously in a high throughput screening system. In this embodiment, multiple assays may be performed in multiple receptacles, such as the wells of a 96 well plate or other multi-well plate. As will be appreciated by one of skill in the art, such a system may be applied to the simultaneous assay of multiple candidate agents.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc. it is understood that the exemplary embodiments provided herein in no way serve to limit the true scope of this invention, but rather are presented for illustrative purposes. All references cited herein are expressly incorporated by reference in their entirety.

Cell and Animal Based Screening Assays for Poxvirus Pathogenesis

Once identified, modulators of poxvirus p28 ligase activity may be tested in cellular and/or non-human animal models for poxvirus pathogenesis.

Such cellular and non-human animal models are generally described in Brick et al, (J. General Virology 81: 1087–1097, 2000), Senkevich et al, (Virology 198: 118–128, 1994) and Senkevich et al, (J. Virology 69: 4103–4111, 1995). As is known in the art, the effect of a candidate agent on a cell or an animal infected with poxvirus may be assayed a number of different ways, including measuring virus titer, replication, infectivity, etc., as well as cellular phenotypes, e.g., proliferation or viability, etc. In particular embodiments, the Moscow strain of ectromelia virus, propagated using BSC-1 cells, may be used.

Any cell that is permissive to poxvirus replication is suitable cells for assaying poxvirus pathogenesis, including COS, HEK-293, BHK, CHO, TM4, CVI, VERO-76, HELA, MDCK, BRL 3A, NIH/3T3 cells, etc. Additional cell lines will become apparent to those of ordinary skill in the art, and a wide variety of suitable cell lines are available from the American Type Culture Collection, 10801 University Boulevard, Manassas, Va. 20110–2209. Cells of particular interest include immune system cells, including lymphocytes (B and T cells e.g., T helper cells) and leucocytes (e.g., granulocytes, lymphocytes, macrophage and monocytes), cells from lymph, spleen and bone marrow tissues, epithelial cells, and cells from or derived from internal organs.

In in vivo assays, any mammal that may be susceptible to poxvirus infection may be used, and in performing assays for poxvirus pathogenesis, any organ or tissue of the mammal may be examined. For example, tissues having immune system cells, e.g., lymph, spleen and bone marrow, tissues from internal organs such as liver, heart, kidney, brain, spleen, etc., and any other tissues, e.g., epithelial tissues from skin, mouth, lungs and internal passages, may be examined.

In one embodiment, p28 ligase activity modulators may be tested to determine if they have an effect on cell viability. In these embodiments, a susceptible cell is transfected with a vector or poxvirus encoding a p28 protein to make it become sensitive to a variety of apoptosis agents, including ultraviolet light (UV), Fas and TNF (Brick et al, supra). The agent is tested to determine if it can protect the transfected cell from those apoptosis agents. In general, apoptosis assays are well known in the art and may be done using standard techniques (e.g., DAPI analysis).

In other embodiments, a susceptible cell, e.g., a macrophage such as a resident peritoneal macrophage, is transfected with a vector or poxvirus encoding a p28 protein to stop dividing or become apoptotic (Senkevich et al, J. Virology 69: 4103–4111, 1995). The agent is then tested to determine if it can increase the viability of the cell or increase cell proliferation. Again, cell viability and cell proliferation assays are well known in the art and may be done using standard techniques.

In other embodiments, a susceptible mammal, e.g., a mouse, may be used for in vivo testing of p28 ligase modulators. If a mouse is used, it may be a pathogen-free mouse of 6–10 weeks of age, or a severe combined immunodeficiency (SCID) mouse (e.g., strain C.B 17). To infect the mice with virus, $5\times10^4$ PFU of ectromelia virus may be injected subcutaneously into their footpads. After 6–10 days, the mice may be sacrificed and assayed for the presence of virus. In most embodiments, viral titer in organs of the mice may be assessed. In particular, viral titer in liver, and/or liver damage may be assessed.

Suitable controls for the above experiments include p28 plasmids or viruses, such as those with an altered ring-finger domain, that are known in the art (Senkevich et al, Virology 198: 118–128, 1994).

Candidate agents possessing poxvirus p28 polypeptide ubiquitin ligase-modulatory activity may be further screened to identify those agents that are specific to the p28 polypeptide by testing the agent in assays that contain other E3 ubiquitin ligases, e.g., cellular ubiquitin ligases such as those listed in literature incorporated by reference above, for example. A "poxvirus p28-specific inhibitory agent" is an agent that inhibits p28 ligase activity without significantly inhibiting the ligase activity of other cellular E3 proteins or other assay components (e.g., E1 or E2 proteins).

Kits

Also provided are reagents and kits thereof for practicing one or more of the above-described methods. The subject reagents and kits thereof may vary greatly. Typically, the kits at least include poxvirus p28 protein or a nucleic encoding such a protein, and other proteins for performing ubiquitylation assays. The subject kits may also include one or more additional reagents, e.g., reagents employed in detecting a label.

In addition to the above components, the subject kits can further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Methods of Reducing Poxvirus Pathogenicity

In another aspect, the invention features methods of reducing poxvirus pathogenicity in a cell by inhibiting the ubiquitin ligase activity of poxvirus p28 protein.

In one embodiment, pathogenicity of a poxvirus in a host cell is reduced by contacting a mammalian cell infected with a poxvirus with an agent that inhibits ubiquitin ligase activity of poxvirus p28 protein in the infected cell, where the agent is provided in amount effective to reduce poxvirus pathogenicity in the cell. The poxvirus may be any poxvirus mentioned above, or a recombinant form thereof.

As discussed above, viral pathogenicity can be determined using a number of different assays, including measuring virus titer, replication, infectivity, transmission, etc., as well as cellular phenotypes, e.g., cell proliferation, viability, expression of markers, etc. Accordingly, the term "pathogenicity" is used herein to indicate any aspect of viral biology that may be measured, including those listed in the previous sentence.

Subjects to be Treated

Any subject having a retroviral infection may be treated according to the invention. Mammalian subjects, especially human subjects, are of particular interest. The terms "individual," "host," "subject," and "patient," used interchangeably herein, refer to a mammal, including, but not limited to, murines, simians, humans, mammalian farm animals, mammalian sport animals, and mammalian pets.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The subjects to be treated thus include those having or at risk of poxvirus infection. The subjects may be symptomatic or asymptomatic. Diseases and symptoms associated with poxvirus infection include, but are not limited to fever, chills, headache, nausea, vomiting severe muscle aches macules, papules, vesicles, pustules and scabbing and other clinical pathologies and symptoms such as bleeding. The methods of the invention can be continued until a desired clinical endpoint is attained (e.g., symptoms diminish or are otherwise improved), viral clearance (e.g. as detected by a decrease in viral titer or undetectably viral titer, etc.).

In particular, the subject invention finds most use for treating, military personnel, healthcare workers, researchers of poxvirus biology, and other persons such as key government officials, since they are at immediate risk from poxvirus, e.g., smallpox, infection.

In particular embodiments, the subject agents may be used to reduce side effects of smallpox vaccine, and, as such, may be administered at the same time as, prior to, or after, administration of such a vaccine.

Formulations and Routes of Administration

Antiviral agents suitable for use in the invention in the methods of inhibiting poxvirus replication (referred to herein as "the agents" or "the active agents" for convenience) as described herein can be formulated in a variety of ways suitable for administration. In general, these compounds are provided in the same or separate formulations in combination with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the agents are formulated separately or in combination, e.g., in an aqueous or non-aqueous formulation, which may further include a buffer. Suitable aqueous buffers include, but are not limited to, acetate, succinate, citrate, and phosphate buffers varying in strength from 5 mM to 100 mM. In some embodiments, the aqueous buffer includes reagents that provide for an isotonic solution. Such reagents include, but are not limited to, sodium chloride, and sugars e.g., mannitol, dextrose, sucrose, and the like. In some embodiments, the aqueous buffer further includes a non-ionic surfactant such as polysorbate 20 or 80.

Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In the subject methods, the active agents may be administered to the host using any convenient means capable of resulting in the desired therapeutic effect. Thus, the agents can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, agents may be administered in the form of their pharmaceutically acceptable salts, or they may also be used alone or in appropriate association, as well as in combination, with other pharmaceutically active compounds. The following methods and excipients are merely exemplary and are in no way limiting.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature. Agents can also be provided in sustained release or controlled release formulations, e.g., to provide for release of agent over time and in a desired amount (e.g., in an amount effective to provide for a desired therapeutic or otherwise beneficial effect).

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the agents calculated in an amount sufficient to produce the desired effect in association with a pharmaceutically acceptable diluent, carrier or vehicle. The specifications for the unit dosage forms for use in the present invention depend on the particular compound employed and the effect to be achieved, the pharmacodynamics associated with each compound in the host, and the like.

Dosage forms of particular interest include those suitable to accomplish intravenous or oral administration, as well as dosage forms to provide for delivery by a nasal or pulmonary route (e.g., inhalation), e.g., through use of a metered dose inhaler and the like.

In general, agents for use in the invention is formulated in either parenteral or enteral forms, usually enteral formulations, more particularly oral formulations. Agents for use in the invention are formulated for parenteral administration, e.g., by subcutaneous, intradermal, intraperitoneal, intravenous, or intramuscular injection. Administration may also be accomplished by, for example, enteral, oral, buccal, rectal, transdermal, intratracheal, inhalation (see, e.g., U.S. Pat. No. 5,354,934), etc.

The invention also contemplates administration of additional agents with the antiviral agents according to the invention, such as other antiviral agents that work through the same of different mechanism.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Abbreviations: The following abbreviations may be used throughout the following examples: VARV, variola virus; ECTV, ectromelia virus; MPV, monkeypox virus; EVP28, ectromelia virus p28; SP28, variola virus (smallpox) p28; eIF4E, eukaryotic initiation factor 4E; KAP1, KRAB-associated protein-1; KRAB, Krüppel-associated box; Ubc, ubiquitin conjugating E2 enzyme; Uev, ubiquitin-conjugating E2 enzyme variant; TRAF6, TNF receptor-associated factor 6; APC, anaphase-promoting complex.

Materials and Methods

Sequence analysis: Sequences of the poxviruses p28 and related viral proteins were extracted from NCBI. Alignment of the three closely related poxvirus sequences was generated by ClustalW.

Cloning and mutagenesis: Synthetic oligonucleotides were designed to assemble the genes encoding EVP28 (p28 of the ectromelia virus, (GenBank accession code NC_004105) or SP28 (p28 of the variola virus, GenBank accession code L22579). The synthetic EVP28 and SP28 genes were cloned into the TA vector (Invitrogen, CA). The Flag tag was then introduced by PCR to engineer N-terminal tagged EVP28 or SP28. Point mutations were introduced at the predicted zinc-coordinating residues (C172A or H198A for EVP28; C173A and/or H199A for SP28) using a Gene Tailor mutagenesis kit (Invitrogen, CA). For mammalian cell expression, genes for Flag-tagged EVP28 or SP28 were cloned into vector pNIG, where the expression of p28 was driven by a strong promoter, the EF-1α promoter.

Recombinant protein expression and purification: The wild-type EVP28, SP28 and their respective RING finger mutants (EVP28 C172A, EVP28H198A, SP28 C173A, and SP28H199A) were cloned into the pFast-Bac expression vector (Invitrogen, CA) with an amino-terminal GST tag. Baculovirus production, protein expression and purification were performed according to the manufacturer's protocols. The following is a brief description of the protocol for the purification of the GST-EVP28 fusion protein. High Five cells (Invitrogen, CA) were inoculated with GST-EVP28 baculovirus at an MOI of 1-10. The infected cells were grown for 40 hours, collected by a 5-minute centrifugation at 2,500 g at 4° C., and then lysed briefly at 4° C. in buffer A (20 mM Tris-HCl, 15% glycerol, 0.5 M NaCl, 2.5 mM EDTA and 1 mM TCEP at pH 8.0) containing protease inhibitors (20 μg/ml PMSF, 2 μM leupeptin, 1 μM pepstatin A). The lysate was sonicated, and clarified by centrifugation at 12,000 g at 4° C. for 40 minutes. The supernatant was mixed with Glutathione agarose beads for 1 hr. The pellet beads with bound GST-EVP28 were washed with buffer B (20 mM Tris-HCl, 15% glycerol, 0.5 M NaCl, 1 mM EDTA, 0.1% NP40 and 1 mM TCEP at pH 8.0), followed by elution with buffer C (20 mM Tris-HCl, 20 mM glutathione, 15% glycerol, 0.05 M NaCl, 1 mM EDTA, 0.01% NP40 and 1 mM TCEP at pH 8.0). The eluted protein was further purified by Q-Sepharose chromatography, and the purity of each fraction was analyzed by SDS-PAGE. Pure p28 fractions were pooled, dialyzed, and stored in aliquots at −80° C. The same protocol was used to purify SP28 and its respective mutants.

Human ubiquitin E1 was expressed as a His-tag fusion protein in insect cells using the same Bac to Bac system (Invitrogen, CA). Different human E2s were expressed as N-terminal GST-tagged fusion proteins in E. coli using the pGex-6p system (Amersham Biosciences, NJ). GST was cleaved following protein purification through a Glutathione column. Ubiquitin was expressed with an amino-terminal Flag-epitope using the expression vector pFlagMac (Sigma, St. Louis), and purified from E. coli.

Cell Fractionation and Western Blot: Approximately $10^7$ HEK 293 cells transfected with pNIG vector or pNIG-SP28 were washed once with PBS, and incubated with 1 mL of PBS containing 0.5% Triton X-100 and 1× protease inhibitor cocktail (Roche Applied Science, Indianapolis) on ice for 15 min. The cellular membrane was disrupted gently with a Dounce tissue grinder (without breaking the nuclear membrane), the lysate was centrifuged at 2,000 rpm for 5 min, and the supernatant collected as the cytoplasmic fraction. The nuclear pellet was washed twice with ice-cold PBS, and then resuspended in 1 mL of PBS containing 05% Triton X-100 and 1× protease inhibitor cocktail. The nuclear membrane was disrupted by sonication for 20 seconds, and the lysate was further incubated on ice for 10 min, and centrifuged at 14,000 rpm for 5 min. The supernatant was collected as the nuclear fraction. To analyze the level of expression and the intracellular distribution of p28, both the cytoplasmic and the nuclear fractions were immunoprecipitated with the anti-Flag antibody as described above, the proteins on beads were eluted with 100 μL of Flag peptide (100 μg/mL, Sigma, St. Louis), and 20 μL of each eluted sample was loaded on a gel and blotted with anti-Flag antibody (1:2000, Sigma, St. Louis).

In vitro Ubiquitin ligase assay: E1 (10 ng), E2 (25 ng), and SP28 or EVP28 (100 ng) were added to a ubiquitin ligase reaction mixture that contained 50 mM Tris-HCl, pH 7.4, 5 mM MgCl$_2$, 0.6 mM DTT, 2 μM ATP, and 100 ng Flag-Ubiquitin. Each 100 μL reaction mixture was incubated at room temperature for 1 hour, and the reaction was stopped by the addition of 4× Laemmli loading buffer, followed by standard SDS-PAGE and Western blot analysis with anti-Flag or anti-GST antibodies.

Example 1

Phylogenetic Analysis of Poxvirus p28 RING Finger Proteins

Figure 1B:
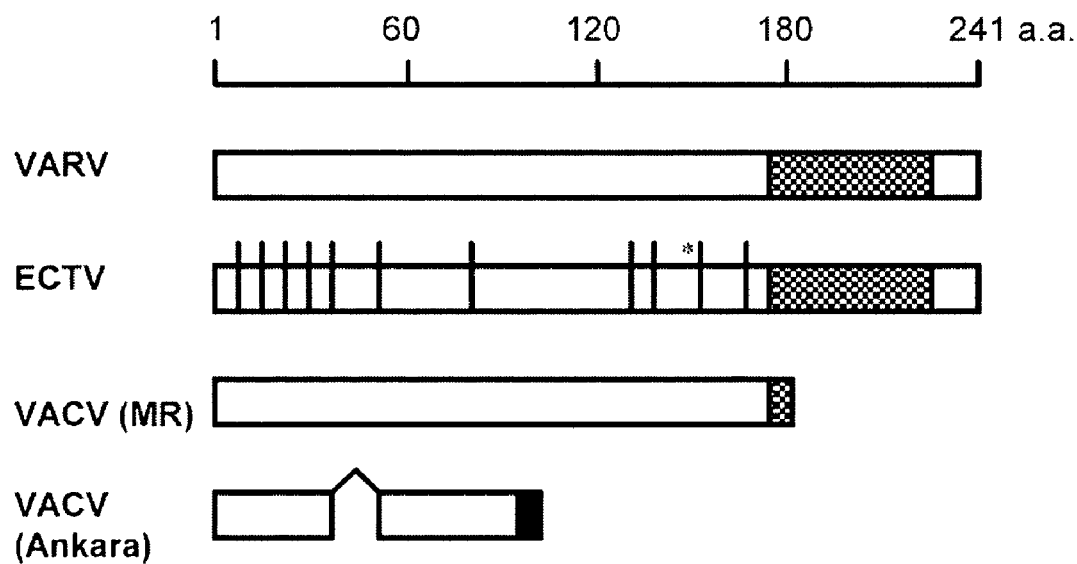
Figure 2A:
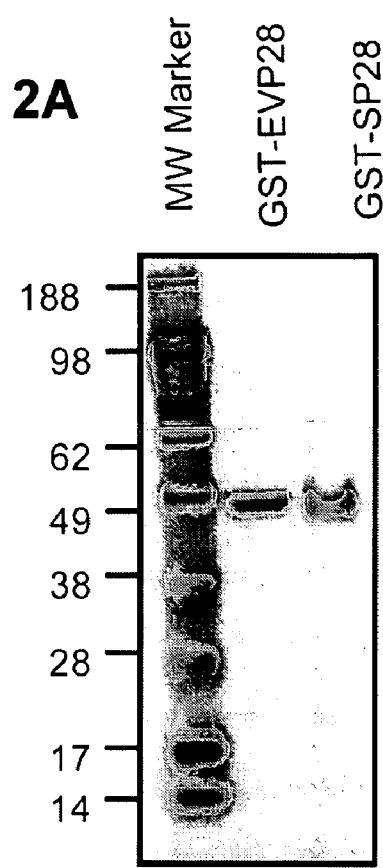
FIGS. 2A and 2B are autoradiographs showing that both ECTV p28 (EVP28) and VARV p28 (SP28) are RING finger E3 ubiquitin ligases. (2A) Purification of recombinant GST-EVP28 and GST-SP28 expressed using the baculovirus expression system. The purity of the proteins was verified by SDS-PAGE analysis and Commassie blue staining. (2B) EVP28 and SP28 possess E3 ubiquitin ligase activity in vitro. Recombinant GST-EVP28 or GST-SP28 was added to an in vitro ubiquitylation reaction containing purified human E1, UbCH5c (E2), and Flag-ubiquitin in the presence of ATP. The formation of poly-ubiquitin chains by p28 was examined by Western blot using an anti-Flag antibody.
Figure 2B:
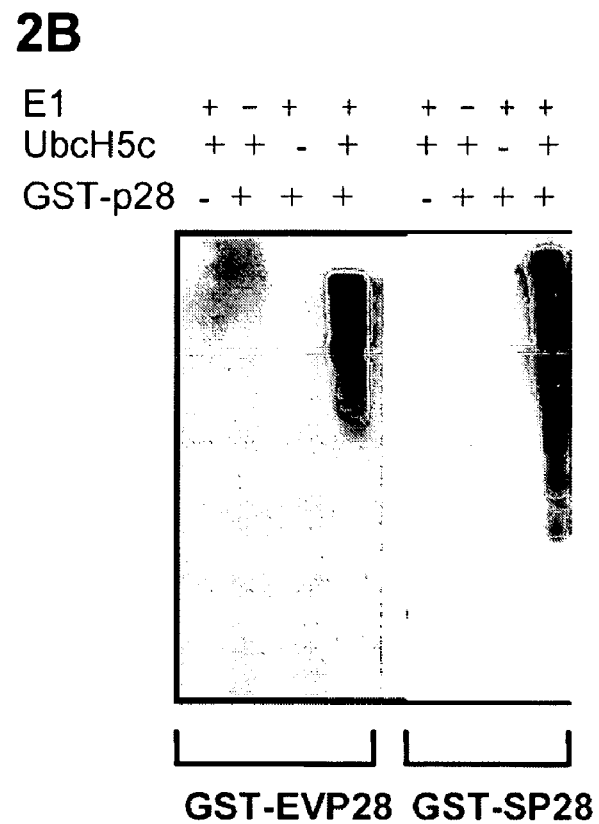
Figure 3A:
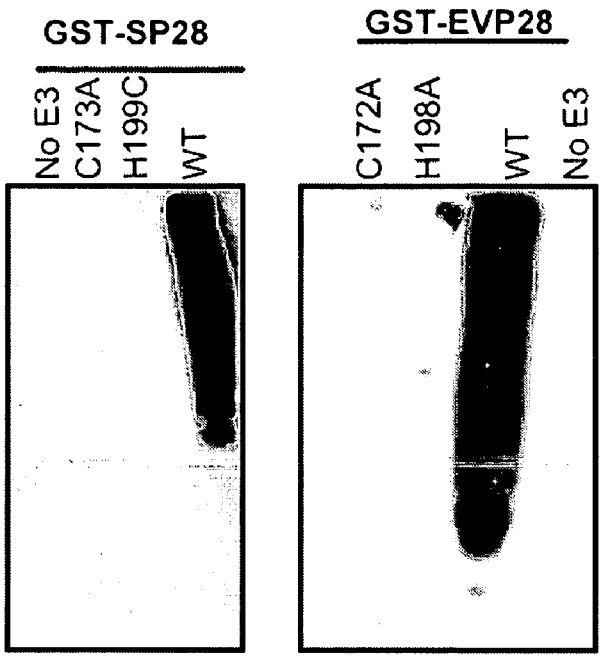
FIGS. 3A–3B are autoradiographs showing that p28 E3 ligase activity is RING-dependent. (3A) Equal amounts of the wild-type VARV p28 (SP28), C173A, or H199A mutants were incubated with E1 and UbCH5c in an in vitro ubiquitylation assay as described in Materials and Methods, and analyzed by Western blot analysis with anti-Flag antibody. The SP28 wild-type, but not the RING mutants, showed E3 ligase activity. (3B) RING-dependent E3 ligase activity associated with ECTV p28 (EVP28), as described in FIG. 3A. (C)SP28 and (D) EVP28 catalyze self-ubiquitylation. Wild-type SP28 or EVP28, as well as their respective mutants (all contain a GST tag at their amino termini), were tested in the in vitro ubiquitylation reaction and analyzed by Western blot using an anti-GST antibody to monitor the formation of poly-ubiquitin chains on SP28, EVP28, and the mutants.
Figure 3B:
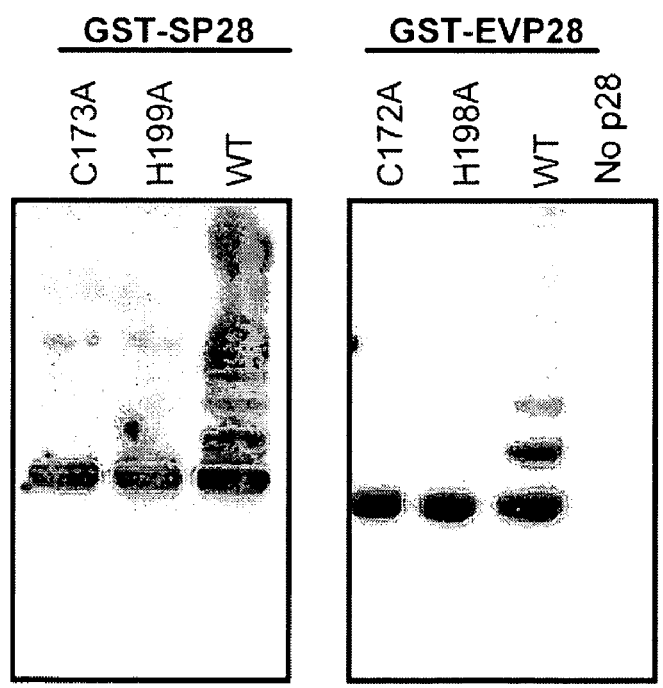
Figure 4A:
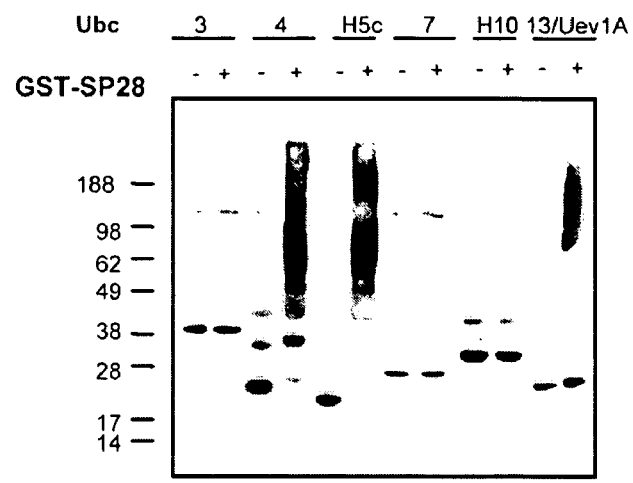
FIGS. 4A–4C are autoradiographs showing that VARV p28 (SP28) and ECTV p28 (EVP28) cooperates with Ubc4, UbCH5c, and Ubc13/Uev1A to catalyze ubiquitylation. (4A) SP28 and (4B) EVP28 have the same E2-selectivity profile. An equal amount of the indicated recombinant E2 was incubated with E1, Flag-ubiquitin, and ATP, in the absence or presence of GST-SP28 or -EVP28, and the formation of poly-ubiquitin chains was examined by Western blot with an antiFlag antibody. (4C) A comparison of SP28 and a few known E3 ligases for competitiveness with Ubc13/Uev1A E2 heterodimer. TRAF6, SP28, MDM2, and APC2/APC11 in equal quantities were added to an in vitro reaction containing Ubc13/Uev1A, E1, Flag-ubiquitin and ATP and incubated at room temperature for one hour. All the reaction products were analyzed by Western blot with an anti-Flag antibody. The data suggest that SP28 and TRAF6, but not MDM2 or APC2/APC11, catalyze poly-ubiquitylation in cooperation with Ubc13/Uev1A.
Figure 4B:
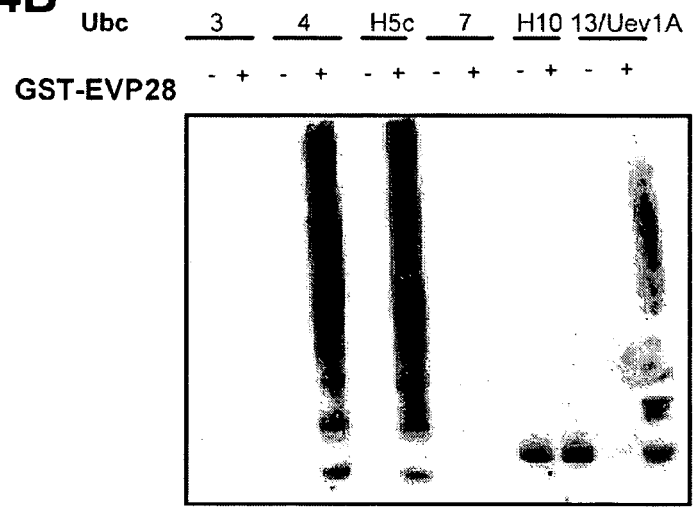
Figure 4C:
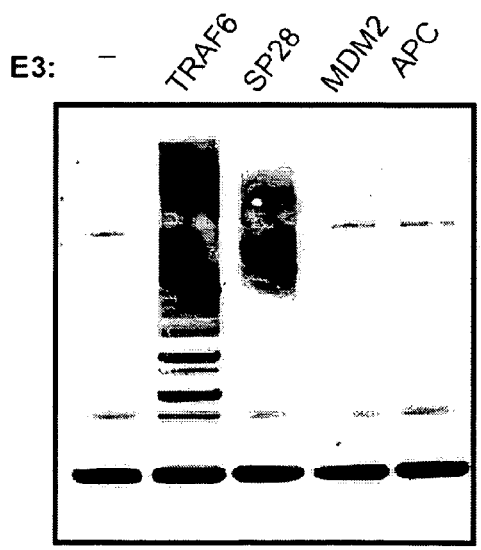

As shown in FIG. 1A, the p28 proteins encoded by genus *Orthopoxviruses* have a high degree of sequence conservation at amino acid level. A high degree of homology is also found in the p28 homologs encoded by genera *Leporipoxvirus* and *Suipoxvirus*, as well as other viruses. In particular, the RING finger domains of the p28 proteins of the "wild-type" orthopoxviruses are almost identical. In contrast, the p28 gene products of culture-adapted VACV isolates contain large deletions that disrupt the RING finger domain (FIG. 1B). Coincidently, VACV infection causes very mild symptoms in humans, a property that enables its use as a live vaccine for smallpox. Further, the RING finger domain of p28 in ECTV has been found to enhance the virulence of the virus by over $10^6$ times in a mouse infection model (Senkevich et al *Virology* 1994 198: 118–128), suggesting that the RING domain of p28, although redundant in cell culture, is associated with ECTV pathogenesis in the host. p28 is thought to play a role in determining virulence of a variety of poxviruses because the sequence of p28 is conserved between those viruses.

The p28 RING finger motif shares the highest homology with the RING finger region of the makorin protein family, whose biological function is unknown. RING fingers are Cys-rich zinc-binding domains identified in over 200 proteins to date. A few discrete biochemical activities have been attributed to RING finger domains. For example, the RING domains of the promyelocytic leukemia protein (PML) and the arenavirus-encoded Z protein bind the translation initiation factor eIF4E and significantly reduce the affinity between eIF4E and the $m^7G$ cap of mRNA, thereby inhibiting mRNA transport and causing translational repression. Kentsis et al (*J Mol Biol* 2001 312, 609–623). In addition, the RING finger domain of KAP1 is critical to the formation of the KAP1:KRAB complex, which mediates transcriptional repression Peng et al (*J Mol Biol* 2000 295, 1139–1162). The conservation of residues between p28 and the cellular RING finger domains is relatively poor with the exception of the seven cysteine and one histidine residues that chelate two zinc atoms.

Example 2

Both ECTV- and VAR V-Encoded p28 Proteins Possess E3 Ubiquitin Ligase Activity p28 expression was achieved by using the baculovirus expression system in which the protein was fused to a GST tag at its amino terminus. Following differential centrifugation, glutathione agarose bead affinity purification, and Q-Sepharose chromatography, the p28 proteins of ECTV and VARV, referred to herein as EVP28 and SP28, respectively, were obtained. The purity of the proteins was verified by SDS-PAGE analysis to be greater than 90% (FIG. 2A).

We examined whether or not the poxvirus p28 virulence factors encoded E3 ligase activity. A substrate-independent in vitro ligase assay was used to monitor the formation of poly-ubiquitin chains in the presence of p28, a method commonly applied to analyze E3 ligases with unknown substrates (Hofmann et al *J Biol Chem* 2001 276, 27936–27943). As shown in FIG. 2B, both GST-EVP28 and GST-SP28 strongly promoted the formation of a high molecular weight ladder/smear on the blot, an indication of ubiquitin polymerization. As expected, the ubiquitin polymerization was not detected in control reactions in which E1, E2, or p28 was excluded (FIG. 2B).

Example 3

The p28 E3 Ligase Activity is RING Finger-Dependent

In order to verify the importance of the RING finger in p28's E3 ligase activity, point mutations were generated at the proposed zinc-binding residues of the RING domain (C173A or H199A in SP28; C172A or H1198A in EVP28). GST-fused mutant SP28 and EVP proteins were purified to near homogeneity using glutathione affinity enrichment followed by Q-Sepharose chromatography, and were tested for their E3 ligase activity in vitro. It was found that a single amino acid substitution at either residue Cys-172/3 or His-198/9 completely abolished the E3 ubiquitin ligase activity of the p28 proteins, suggesting that the integrity of the RING finger domain is critical for its ligase activity (FIG. 3A).

It has been shown that RING finger E3 ligases can mediate auto-ubiquitylation, substrate ubiquitylation, as well as the formation of unanchored poly-ubiquitin chains in vitro. Western blot using a GST antibody was performed to determine whether p28 underwent auto-ubiquitylation in the biochemical reaction. Indeed, the formation of high molecular weight GST-SP28 or GST-EVP was readily detected in the blot, suggesting that a substantial portion of the poly-ubiquitin chains formed in the biochemical assay were the product of p28 auto-ubiquitylation (FIG. 3B). Consistent with the null phenotype of RING finger point mutants, p28 bearing either C172/3A or H198/9A mutations showed no auto-ubiquitylation activity (FIG. 3B).

Example 4 p28 Cooperates with Different E2s to Catalyze Ubiquitylation

To determine which E2s could cooperate with SP28 or EVP28, six different recombinant E2s were tested in the in vitro ligase assay. It was found that three of the E2s, Ubc4, UbCH5c, and Ubc13/Uev1A, were capable of working with p28 to promote poly-ubiquitin chain formation (FIGS. 4A and 4B). Ubc4 and UbCH5c share about 97% identity in protein sequence and have been shown to participate in catalyzing Lys-48 linked polyubiquitylation for proteasome recognition and subsequent protein degradation (Pickart et al *Nat Struct Biol* 2000 7, 999–1001). The heterodimeric Ubc13/Uev1A has been shown to work with a smaller subset of E3 ligases and plays a unique role in promoting the formation of Lys-63 linked multi- or poly-ubiquitin chains for a variety of cellular functions such as kinase activation) Deng et al Cell 2000 103, 351–361), regulation of ribosome activity (Spence *Cell* 2000 102, 67–76), and endocytosis (Galan et al *Embo J* 1997 16, 5847–5854). We thus compared SP28 and several well-characterized E3 ligases for their compatibility with Ubc13/Uev1A. Among these ligases, TRAF6 and SP28 cooperated well with Ubc13/

Uev1A, whereas MDM2 and APC2/APC11 did not (FIG. 4C). The finding that SP28 and EVP28 can cooperate with different E2s demonstrates that p28 is involved in both Lys-48 and Lys-63 linked ubiquitin polymerization and therefore may impact multiple cellular activities.

Example 5 p28 Catalyzes the Formation of Lys-63 Linked Polyubiquitin Chains

Figure 5:
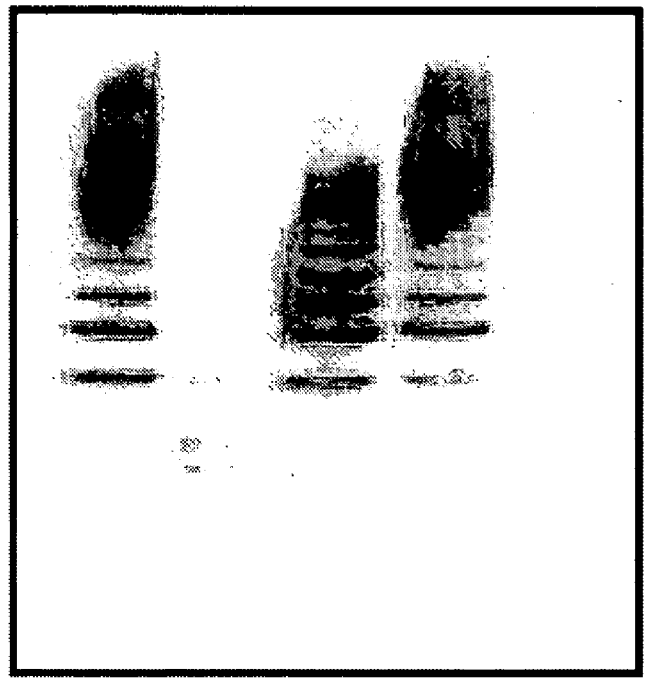
FIG. 5 are autoradiographs showing that VARV p28 (SP28) catalyzes the formation of Lys-63 linked poly-ubiquitin chains. The wild-type (Lane 1) and mutant ubiquitins (Lanes 2–5), all tagged with a Flag epitope at the amino-terminus, were added to a substrate-independent in vitro ubiquitylation reaction mixture containing human E1, Ubc13/Uev1A as E2, GST-SP28, and ubiquitylation buffer. K48 (Lane 2) and K63 (Lane 3) denote ubiquitin mutants containing Lys-48 or Lys-63 as the sole Lys residue, respectively. K48R (Lane 4) and K63R (Lane 5) denote ubiquitin mutants with a single Lysine-to-Arginine substitution at amino acid position 48 and 63, respectively. With Ubc13/Uev1A as E2, SP28 selectively catalyzed the formation of poly-ubiquitin chains via residue Lys-63 of ubiquitin.

Ubiquitin is one of the most highly conserved proteins in eukaryotes, and the 76-amino acid long human and mouse isoforms are identical. There are 7 Lys residues in human/mouse ubiquitin, including Lys-48 and Lys-63. Poly-ubiquitin chains linked via Lys-48 are structurally distinct from those linked via Lys-63, which might be the basis for their differential biological functions (Varadan et al *J Biol Chem* 2004 279, 7055–7063). To further investigate the possibility of Lys-63 linked ubiquitin chain formation by p28 E3 ligase and the heterodimeric Ubc13/UevA E2 complex, the in vitro ligase assay was performed using different forms of ubiquitin. As shown in FIG. 5, with Ubc13/UevA as an E2, SP28 catalyzed poly-ubiquitin chain formation in the presence of either wild-type ubiquitin or a mutant ubiquitin that contains only a single Lys residue at position 63 (K-63 only). In contrast, the formation of poly-ubiquitin chains was dramatically reduced in the same reaction using a mutant ubiquitin containing a single Lys residue at position 48 (K-48 only). Furthermore, a Lys-63 to Arg substitution in ubiquitin (K63R) abolished the generation of poly-ubiquitin chains by SP28, while replacing Lys-48 with an Arg residue had no significant effect (K48R). EVP28 displayed the same ubiquitin recognition profile in assays using Ubc13/Uev1A heterodimeric E2 (data not shown). Our observations demonstrate that the poxvirus p28 E3 ligase is capable of catalyzing Lys-63 linked poly-ubiquitylation in concert with Ubc13/UevA. These results demonstrate that p28 ligases not only mediate their target protein(s)' proteolytic destruction, but may also play a role in functional regulation through a unique Lys-63 linked polyubiquitylation.

Example 6 p28 E3 Ligase Activity in Transfected Mammalian Cells

Figures 6A, 6B, 6C:
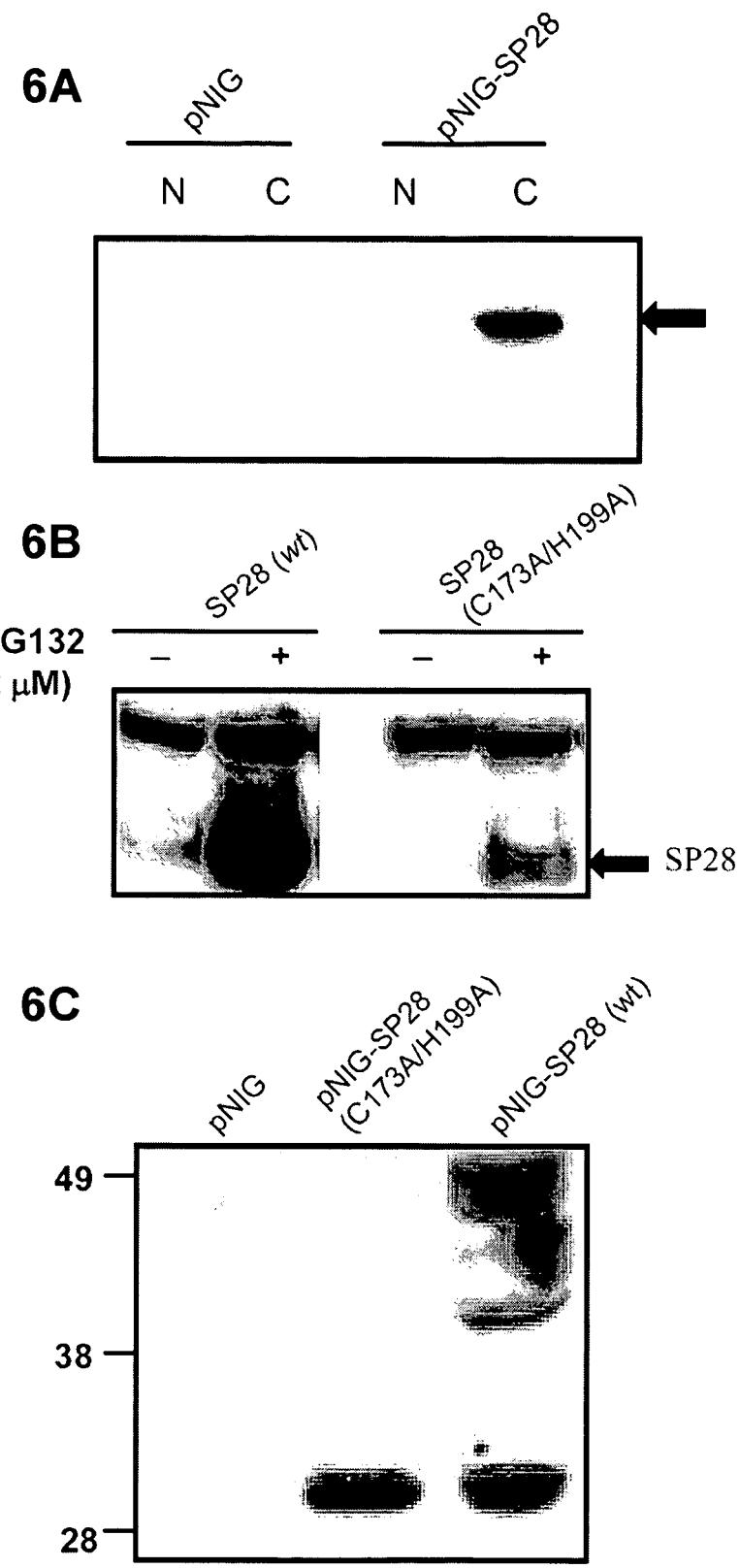
FIG. 6A–6C are autoradiographs. (6A) Subcellular localization of VARV p28 (SP28). HEK293 cells were transfected with pNIG vector or pNIG-SP28 for 24 hours, treated with 2 µM MG132 for 6 hrs, and then homogenized in lysis buffer (see Materials and Methods). Each cell lysate was fractionated into cytoplasmic (C) and nuclear (N) fractions by differential centrifugation, and analyzed by Western blot using an anti-Flag antibody. SP28 was mainly detected in the cytoplasmic fraction of the cell lysate. (6B) SP28 undergoes proteasome-dependent degradation. HEK 293 cells transfected with either SP28 wild-type or the mutant (C173A/H199A) were treated for 6 hours with DMSO control or 2 µM MG132 at 24 hours post transfection. The cells were lysed, and each lysate was subjected to electrophoresis in denaturing gels and probed with the anti-Flag antibody. MG132 stabilize both the wild-type and the mutant SP28, but the stabilizing effect on the wild-type is more pronounced, suggesting SP28 catalyzed self-ubiquitylation in cells. The Flag antibody reacts with a non-specific protein above SP28, which serves here as a loading control. (6C) Evidence of SP28 self-ubiquitylation in mammalian cells. HEK 293 cells transfected with either the wild-type SP28 or the C173A/H199A mutant were treated with 2 µM MG132 for 6 hrs before harvest. Boiling 1× lysis buffer were added to cell pellets, mixed, and immediately heated at 95° C. for 5 min. Genomic DNA in the samples was subsequently sheared with 251/2 gauge needles. The cell lysates were analyzed by Western blot probed with p28 polyclonal antibody.

To verify that SP28 has ubiquitin E3 ligase activity in vivo, HEK293 cells were transfected with a Flag-tagged SP28 expression vector, pNIG-Flag-SP28. Twenty-four hours after transfection, cells were treated with 2 μM MG132, a proteasome inhibitor, for 6 hours, and then lysed in a buffer containing 10 μM MG132 in order to reduce 26S proteasome-mediated degradation of SP28. The lysate was further fractionated by differential centrifugations into cytoplasmic and nuclear fractions. The samples were immunoprecipitated with an anti-Flag antibody, separated on an SDS-PAGE gel, and blotted with anti-p28 antibody to reveal the subcellular localization of SP28. As shown in FIG. 6A, SP28 was mainly detected in the cytoplasmic fraction of the cell lysate, an observation confirming a previous report that p28 is expressed as a cytosolic protein during ECTV infection. Moreover, treating SP28 expressing cells with the proteasome inhibitor MG132 remarkably enhanced stability of wild-type SP28 (FIG. 6B). The SP28 mutant with C173A/H199A substitutions, shown to have a null phenotype in E3 ligase assays, was also stabilized by MG132, although to a much lesser extent (FIG. 6B). A similar effect of MG132 on EVP28 was also observed (data not shown). The pronounced stabilization of wild-type p28 by MG132 demonstrates that SP28 is an active E3 ubiquitin ligase in cells. To further prove that SP28 expressed in mammalian cells encodes E3 ubiquitin ligase activity, HEK293 cells were transfected with pNIG vectors expressing either wild-type SP28, or its RING finger mutant (SP28 C173A/H199A), both tagged with an amino-terminal Flag-epitope. The cells were lysed in boiling lysis buffer to preserve poly-ubiquitin chains from degradation by deubiquitinating enzymes (DUBs) or proteases. The lysates were then analyzed by Western blot using a p28 polyclonal antibody. The results demonstrate that wild-type SP28, but not the C173A/H199A mutant, forms ubiquitin ladders in transfected cells (FIG. 6C). Thus the poxvirus p28 virulence factor encodes an E3 ubiquitin ligase that has activity in mammalian cells, and there is substantial SP28 self-ubiquitylation in cells as well as in biochemical assays.

In summary, the results described above demonstrate that the poxvirus p28 virulence factor encodes an E3 ubiquitin ligase. p28 mutants lacking one of the proposed zinc-binding residues (C173A or H199A in SP28; C172A or H198A in EVP28) lose their ligase activity, confirming the crucial role of the RING finger domain in the enzymatic process. p28 is capable of catalyzing the formation of both Lys-48 and Lys-63 linked poly-ubiquitin chains. p28 triggers Lys-63 linked poly-ubiquitylation in concert with Ubc13/Uev1A heterodimeric E2. p28 may interfere with cellular antiviral mechanisms, such as immune/inflammatory responses and apoptosis, through Lys-63 linked ubiquitylation of itself or its protein substrate(s).

Example 7

E3 Ligase Assay with Different E2 Conjugating Enzymes

HEK 293 cells were transfected with either HA-p28 or HA-MDM2 expression plasmid. Forty eight hours after transfection, the cells were lysed, and each lysate was immunoprecipitated (IP'd) with an anti-HA tag antibody. The IP'd materials were tested for E3 ligase activity in vitro using a FLAG-tagged ubiquitin. After separating the assay products using electrophoresis, the products were detected by blotting using an anti-FLAG antibody. A ladder of products, indicating polyubiquitination, was observed. These results are shown in FIGS. 7A, 7B and 8.

Figures 7A, 7B:
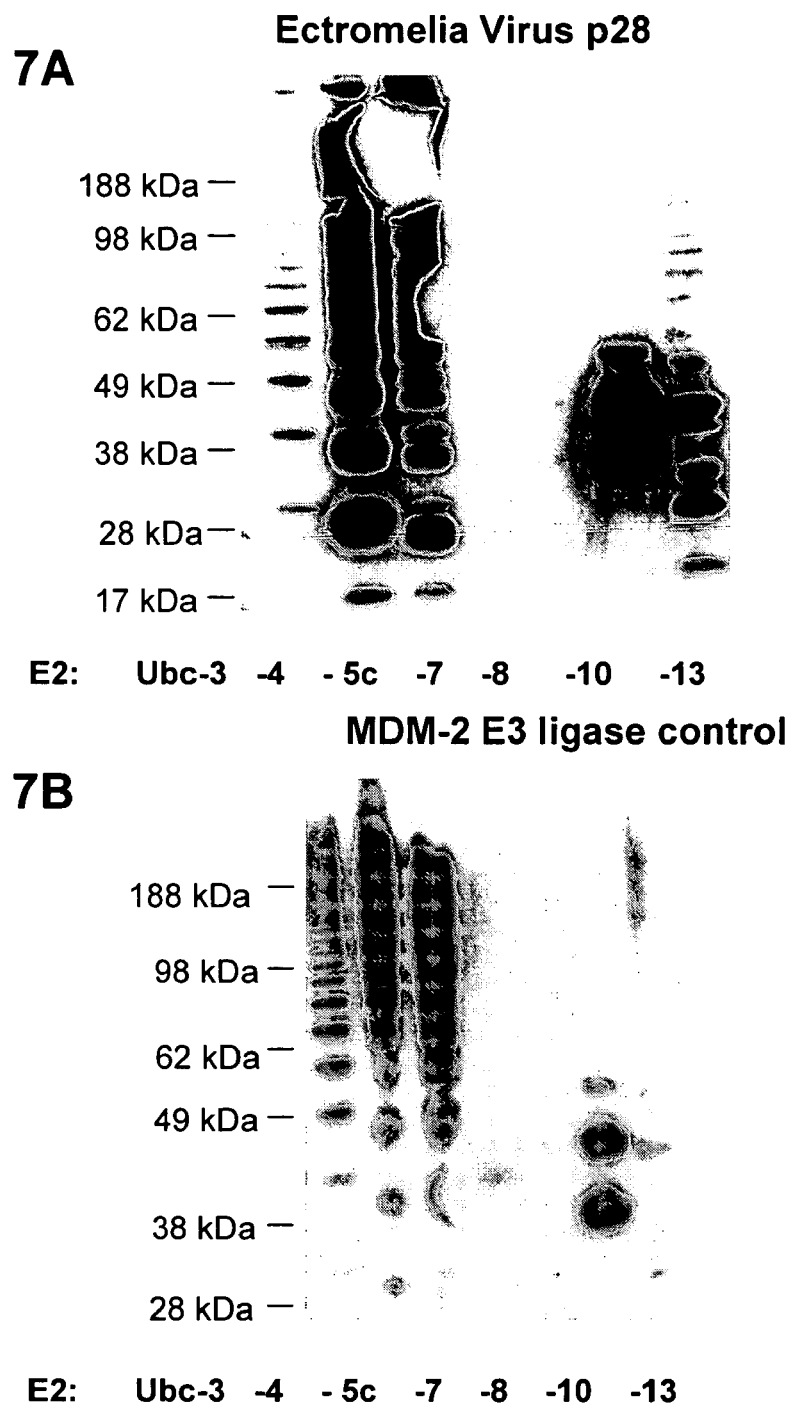
FIGS. 7A and 7B are autoradiographs showing the activity of p28 as an E3 ligase with various human E2 conjugating enzymes. Panel A shows the accumulation of poly-ubiquitin on p28, after performing the assay described in Example 1. Panel B shows the accumulation of poly-ubiquitin on a human E3, MDM-2, under similar conditions. HEK 293 cells were transfected with either HA-p28 or HA-MDM expression plasmid. Forty-eight hours after transfection, the cells were lyzed, and each lysate was immunoprecipitated (IP) with an anti-HA tag antibody. The IP materials were tested for their E3 ligase activity in vitro. The results show that EV p28, a poxvirus-encoded RING finger protein, was a E3 ligase. EV p28 was active in the presence of Ubc-4, -5, and -13. (Ubc-3, and -10 catalyzed polyubiquitin chain formation without E3.

The results shown in FIGS. 7A and 7B show that EV p28, a poxvirus-encoded RING finger protein, is a E3 ubiquitin ligase (7A). EV p28 was active in the presence of Ubc-4, -5 and -13. MDM-2 is a positive control in these assays (7B).

Figure 8:
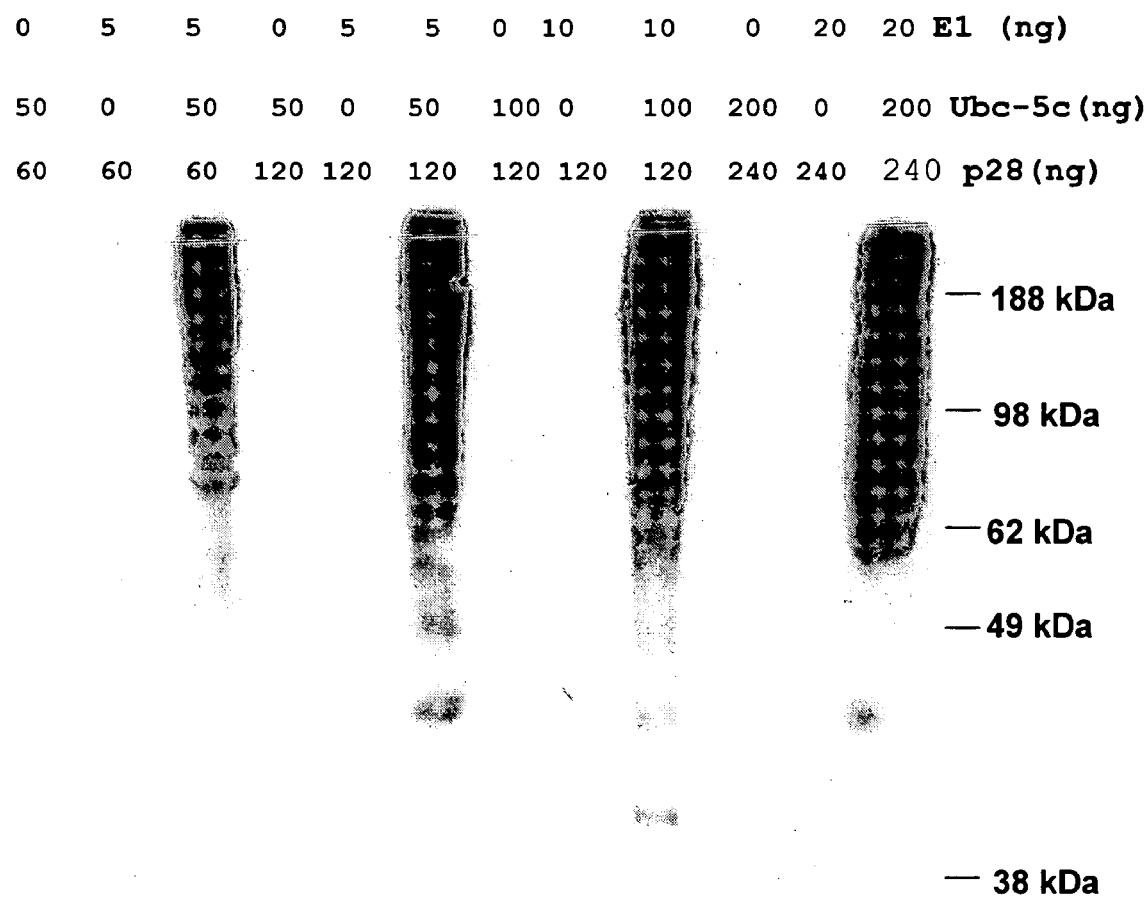
FIG. 8 shows the accumulation of poly-ubiquitin on p28, after performing the assay described in Example 1, in the presence of varying concentrations of E1, E2 and E3. The presence of all three components of the ubiquitination cascade are required for activity, and the extent of polyubiquin accumulation varies with the amount of p28 present.

FIG. 8 shows the results of a titration of poxvirus p28 and ubc-5c in vitro. Poxvirus p28 is active at amounts as low as 60 ng per reaction.

Example 8

Poxvirus p28 Protein Ubiquitin Ligase Activity Requires the Poxvirus p28 Protein Zinc Finger Two EV p28 mutants were made, "Evp28C173A" and "Evp28H199C" in which the cys and his residues of the p28 RING-finger domain (a type of Zn-finger of 40 to 60 residues that binds two atoms of zinc), were altered to ala and cys, respectively.

Figure 9:
FIG. 9 shows the results of an assay that demonstrates that C172 and H198 are required for p28 ubiquitin ligase activity.

When assayed, these p28 mutants had no significant ubiquitin ligase activity. The results of this assay are shown in FIG. 9.

Example 9

In Vitro Ubiquitin Ligase Assay Screening Methods

The wells of GST plates were blocked with 100 µl of 1% casein in PBS for 1 hour at room temperature, and then washed three times with 200 µl PBS. To each well, 80 µl of reaction buffer (62.5 mM Tris pH 7.6 [Trizma Base-Sigma T-8524], 3 mM $MgCl_2$ [Magnesium Chloride], 1 mM DTT [Sigma D-9779] and 2 µM ATP [Riche Boehringer Mann Corp-635-316] and 100 ng/well of Flag-ubiquitin was added. 10 µl of candidate agent dissolved in DMSO was added, and 10 µl of E1, E2 and EV p28 was added in protein buffer (20 mM Tris pH 7.6, 10% glycerol [Sigma G5516] and 1 mM DTT). The corresponds to about 10 ng E1, 10 ng Ubc5c and 25 ng of EVP28, and 100 ng of flag ubiquitin.

The mixture is shaken for 10 minutes and then incubated at room temperature for 1 hour. After incubation, the wells were washed three times with 200 µl of PBS, and 10011 of anti-Flag (1:30,000) and anti-mouse Ig-HRP (1:150,000) in 0.25% BSA/PBS were added to each well. This mixture is incubated at room temperature for 1 hr.

After incubation, the wells are washed three times in 200 µl of PBS. After washing, 100 µl of Lumino substrate (1:5 dilution) is added to the wells, and the plates are read in a Lumino Image Analyzer.

Figure 10:
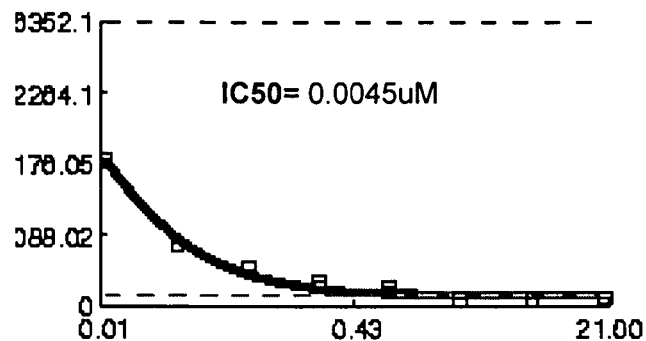
FIG. 10 is a compilation of three graphs showing inhibitors of p28 ubiquitin ligase activity.
Figure 10:
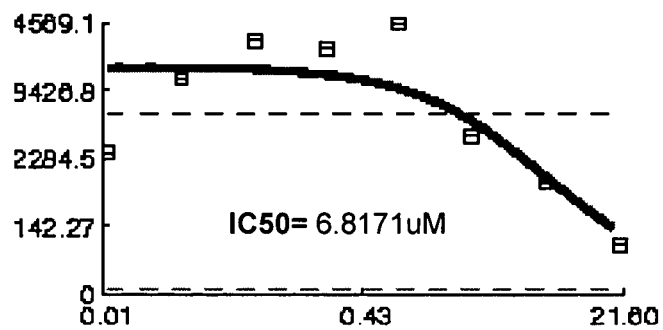
Figure 10:
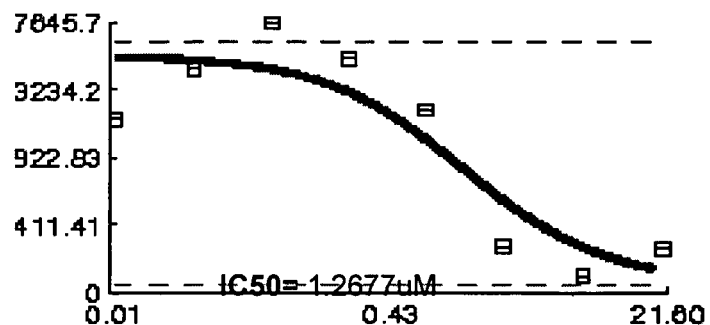

A library of small (i.e., under 500 Da in size) organic compounds that contained known inhibitors of ubiquitylation was screened using these the methods set forth above. Agent titration graphs, showing the amount of ubiquitylation on the vertical axis and the amount of compound on the horizontal axis, are shown in FIG. 10. Horizontal dotted lines at the top and bottom of each graph indicate negative and positive controls, respectively. Three active compounds were identified. Compound 1, described in U.S. provisional patent application Ser. No. 60/514,951, entitled "Rhodanine Compositions for use as Antiviral Agents", filed on Oct. 28, 2003, inhibited ubiquitylation with a IC50 of 4.5 nM. In controls assays, using two ubiquitin ligases that were not a poxvirus p28 polypeptide, the same compound was active at an $IC_{50}$ of 75 nmol and 35 nmol, respectively, indicating that this compound is an specific inhibitor of the ubiquitin ligase activity of poxvirus p28 polypeptide. Compound 2 is described in U.S. provisional patent application 60/475,223, entitled "Ubiquitin Ligase Inhibitors" filed on May 30, 2003 and inhibited ubiquitylation with a $IC_{50}$ of 6.8 µM. Compound 2 also inhibited ubiquitylation when other ubiquitin ligases were used in the screening assays at a $IC_{50}$ of approximately 6 µM, indicating that compound 2 is a non-specific inhibitor of ubiquitin ligases. Compound 3 is described in U.S. provisional patent application Ser. No. 60/509,780 entitled "Ubiquitin Ligase Inhibitors", filed on $9^{th}$ Oct. 2003, and inhibited ubiquitylation at an $IC_{50}$ of 1.2 µM. Compound 3 inhibits the ubiquitin activating activity of the E1 protein used in this assay.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of ubiquitylating a substrate, comprising:
combining an E1 polypeptide, an E2 polypeptide, ubiquitin and a poxvirus P28 protein having an amino acid that is at least 80% identical to a p28 protein encoded by the genome of an orthopoxvirus under ubiquitylation reaction conditions; and
detecting a ubiquitylated substrate.

2. The method of claim 1, wherein said ubiquitylated substrate is autoubiquitylated p28 polypeptide.

3. The method of claim 1, wherein said ubiquitylated substrate is a polyubiquitinated substrate.

4. The method of claim 1, wherein said ubiquitylated substrate is a cognate poxviral polypeptide or a host-cell polypeptide.

5. The method of claim 1, wherein said method is conducted in a cell as a cell-based method.

6. The method of claim 1, wherein said method is a cell-free ubiquitylation method.

7. The method claim 1, wherein said method is performed in the presence of a test agent.

8. The method of claim 1, wherein said poxvirus P28 protein has an amino acid that is at least 95% identical to a p28 protein encoded by a variola virus genome.

9. The method of claim 1, wherein said poxvirus P28 protein has an amino acid that is identical to a p28 protein encoded by a variola virus genome.

10. A method for identifying an inhibitor of poxvirus p28 polypeptide ubiquitin ligase activity, comprising:
contacting a poxvirus p28 polypeptide having an amino acid that is at least 80% identical to a p28 protein encoded by the genome of an orthopoxvirus with a candidate agent in the presence of ubiquitin under ubiquitylation reaction conditions; and
determining an effect of said agent on a ubiquitin ligase activity of said p28 polypeptide;
wherein the effect of the candidate agent upon said ubiquitin ligase activity is indicative of its inhibitory effect.

11. The method of claim 10, wherein said activity is a polyubiquitylation activity.

12. The method of claim 10, wherein said activity is an autoubiquitylation activity.

13. The method of claim 10, wherein said method further comprises:
contacting said candidate agent with cells comprising said poxvirus p28 polypeptide and ubiquitin; and
determining an effect of said agent on said cells.

14. The method of claim 13, wherein said cells are tested for p28-induced cell death.

15. The method of claim 13, wherein said cells are tested for UV-induced apoptosis.

16. The method of claim 13, wherein the said cells are tested for p28-mediated antagonism of cytokine activation.

17. The method of claim 16, wherein said cyctokines include a tumor necrosis factor and an interferon.

18. The method of clam 10, wherein said method further comprises contacting said candidate agent with a poxvirus-infected cell.

19. The method of clam 10, wherein said method further comprises testing said candidate agent on a poxvirus-infected mammal.

20. The method of clam 19, wherein said mammal is a non-human animal model of poxvirus infection.

21. The method of claim 10, wherein said method includes combining an E1 polypeptide, an E2 polypeptide, ubiquitin and a poxvirus P28 protein under ubiquitylation reaction conditions in the presence of a test agent.

22. The method of claim 21, wherein said E1 polypeptide is human ubiquitin E1.

23. The method of claim 21, wherein said E2 polypeptide is Ubc4, UbcH5 or Ubc13.

24. The method of claim 10, wherein said method is a cell-based method.

25. The method of claim 10, wherein said method is a cell-free method.

26. The method of claim 10, wherein said poxvirus P28 protein has an amino acid that is at least 95% identical to a p28 protein encoded by a variola virus genome.

27. The method of claim 10, wherein said poxvirus P28 protein has an amino acid that is identical to a p28 protein encoded by a variola virus genome.

28. A method for identifying a target for the treatment of a poxvirus infection, comprising, contacting a poxvirus p28 polypeptide having an amino acid that is at least 80% identical to a p28 protein encoded by the genome of an orthopoxvirus with a candidate cellular polypeptide in the presence of ubiquitin and under condition suitable for p28 ubiquitylation activity; and, determining if said polypeptide is ubiquitylated by said p28 polypeptide;

wherein a cellular polypeptide that is ubiquitylated by said p28 polypeptide is a target for modulation to effect treatment of a poxvirus infection in a cell.

29. The method of claim 28, wherein said method is a cell-based method.

30. The method of claim 28, wherein said method is an in vitro polyubiquitylation assay.

31. The method of claim 28, wherein said poxvirus P28 protein has an amino acid that is at least 95% identical to a p28 protein encoded by a variola virus genome.

32. The method of claim 28, wherein said poxvirus P28 protein has an amino acid that is identical to a p28 protein encoded by a variola virus genome.

* * * * *